United States Patent
Imamura et al.

(10) Patent No.: US 8,888,704 B2
(45) Date of Patent: Nov. 18, 2014

(54) ULTRASOUND IMAGING APPARATUS AND METHOD FOR DISPLAYING ULTRASOUND IMAGE

(75) Inventors: Tomohisa Imamura, Nasushiobara (JP); Kazuya Akaki, Nasushiobara (JP); Atsushi Sumi, Otawara (JP); Akihiro Kakee, Nasushiobara (JP); Takuya Sasaki, Nasu-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 475 days.

(21) Appl. No.: 12/477,230

(22) Filed: Jun. 3, 2009

(65) Prior Publication Data
US 2009/0306514 A1 Dec. 10, 2009

(30) Foreign Application Priority Data

Jun. 10, 2008 (JP) ................. 2008-151675

(51) Int. Cl.
| | |
|---|---|
| *A61B 8/00* | (2006.01) |
| *G06K 9/00* | (2006.01) |
| *G01S 7/52* | (2006.01) |
| *A61B 8/14* | (2006.01) |

(52) U.S. Cl.
CPC ............ *A61B 8/463* (2013.01); *G01S 7/52073* (2013.01); *A61B 8/461* (2013.01); *A61B 8/464* (2013.01); *G01S 7/52074* (2013.01); *A61B 8/462* (2013.01); *A61B 8/14* (2013.01)
USPC ........................................ 600/443; 382/128

(58) Field of Classification Search
USPC .................. 600/437, 443, 458; 382/128, 130; 715/764
See application file for complete search history.

(56) References Cited

U.S. PATENT DOCUMENTS

| | | | |
|---|---|---|---|
| 2003/0176792 A1 | 9/2003 | Kawagishi et al. | |
| 2006/0086187 A1 | 4/2006 | Kawagishi et al. | |
| 2006/0184019 A1* | 8/2006 | Ito et al. ........................ | 600/437 |
| 2007/0230758 A1 | 10/2007 | Fan et al. | |
| 2008/0246724 A1* | 10/2008 | Pan et al. ...................... | 345/157 |

FOREIGN PATENT DOCUMENTS

| | | |
|---|---|---|
| CN | 1454570 A | 11/2003 |
| CN | 1644169 A | 7/2005 |
| CN | 1785124 A | 6/2006 |
| CN | 101057785 A | 10/2007 |
| CN | 101069647 A | 11/2007 |
| CN | 101147687 A | 3/2008 |

(Continued)

OTHER PUBLICATIONS

Office Action issued Oct. 12, 2010 in Chinese Application No. 200910146613.5.

(Continued)

*Primary Examiner* — Michael Rozanski
(74) *Attorney, Agent, or Firm* — Oblon, Spivak, McClelland, Maier & Neustadt, L.L.P.

(57) ABSTRACT

An imaging part acquires a plurality of ultrasound image data by sequentially imaging the subject with ultrasound waves. A display controller causes a display to display, side by side, a plurality of ultrasound images based on the plurality of ultrasound image data acquired by the imaging part.
Moreover, the display controller causes the display to display measurement markers for obtaining quantitative information of tissues shown in the ultrasound images in a state superimposed in relatively the same positions on the plurality of ultrasound images.

14 Claims, 19 Drawing Sheets

(56) References Cited

FOREIGN PATENT DOCUMENTS

| JP | 62-4978 | | 1/1987 |
| JP | 3-106356 | A | 5/1991 |
| JP | 5-15531 | A | 1/1993 |
| JP | 6-292666 | | 10/1994 |
| JP | 9-201359 | A | 8/1997 |
| JP | 10-105729 | A | 4/1998 |
| JP | 11-221216 | | 8/1999 |
| JP | 2000-321306 | A | 11/2000 |
| JP | 2003-79620 | A | 3/2003 |
| JP | 2003-230559 | A | 8/2003 |
| JP | 2004-208858 | A | 7/2004 |
| JP | 2005-296436 | A | 10/2005 |
| JP | 2005-334089 | A | 12/2005 |
| JP | 2006-158799 | | 6/2006 |
| JP | 2006-187484 | A | 7/2006 |
| JP | 2007-275588 | A | 10/2007 |

OTHER PUBLICATIONS

Japanese Office Action issued Nov. 13, 2012 in Patent Application No. 2008-151675.
Office Action issued Feb. 5, 2013 in Japanese Patent Application No. 2008-151675.
Combined Chinese Office Action and Search Report issued Dec. 19, 2013 in Patent Application No. 201210241662.9 with English Translation of Category of Cited Documents.

* cited by examiner

ULTRASOUND IMAGING APPARATUS AND METHOD FOR DISPLAYING ULTRASOUND IMAGE

BACKGROUND OF THE INVENTION

1. Field of the Invention

The present invention relates to an ultrasound imaging apparatus that transmits ultrasound waves to the subject, generates an ultrasound image based on reflected waves from the subject and displays the ultrasound image, and also relates to a method for displaying an ultrasound image. In particular, the present invention relates to an ultrasound imaging apparatus that obtains quantitative information of tissue shown in an ultrasound image, and also relates to a method for displaying an ultrasound image.

2. Description of the Related Art

An ultrasound imaging apparatus transmits ultrasound waves to the subject and generates ultrasound image data representing the morphology of tissue within the subject based on reflected waves from the subject. An ultrasound imaging apparatus according to a conventional art has a function of measuring the size of tissue such as a lesion site and organ shown in an ultrasound image. For example, the ultrasound imaging apparatus is provided with a function of measuring the distance between two points in tissue like a lesion site, a function of measuring the perimeter of tissue, a function of measuring the area of tissue, etc.

In the abovementioned measurement functions, a measurement marker called a measurement caliper is displayed on an ultrasound image. This measurement caliper can be moved on a screen with an input device such as a trackball. An operator fits the position of the measurement caliper to the position of a site to be measured shown in an ultrasound image. The ultrasound imaging apparatus obtains a quantitative value by measuring the size of tissue designated with the measurement caliper. For example, it is possible to designate two points on an ultrasound image with the measurement caliper to measure the distance between the designated two points.

Further, a plurality of ultrasound images may be displayed side by side to measure the size of a measurement target shown in each of the ultrasound images. For example, in the case of simultaneous display of two ultrasound images, conventionally, a measurement caliper is displayed on one of the ultrasound images, and the operator moves the measurement caliper to the position of a measurement target to measure the size of the measurement target shown in the one ultrasound image. Next, the measurement caliper is displayed on the other ultrasound image, and the operator moves the measurement caliper to the position of a measurement target to measure the size of the measurement target shown in the other ultrasound image. Thus, conventionally, the measurement is executed by individually operating the measurement caliper in each of the ultrasound images and designating a measurement target shown in each of the ultrasound images.

Further, there is a known method of displaying a B-mode image captured in the B-mode and an M-mode image captured in the M-mode side by side to obtain the quantitative value of a measurement target shown in the B-mode image in a case that a measurement caliper is on the B-mode image whereas obtain the quantitative value of a measurement target shown in the M-mode in a case that the measurement caliper is on the M-mode image (Japanese Examined Patent Publication No. 62-4978).

Further, there is a method of simultaneously displaying two ultrasound images, and displaying a cursor in a designated position on one of the ultrasound images, whereas displaying another cursor on the other ultrasound image in a position corresponding to the designated position on the one ultrasound image (Japanese Unexamined Patent Publication No. 11-221216).

However, in the case of simultaneously displaying a plurality of ultrasound images, it is difficult for the operator to grasp the positional relation between the images. Therefore, it is difficult for the operator to observe a plurality of ultrasound images, move a measurement caliper to positions corresponding to each other on the plurality of ultrasound images, and measure the size of measurement targets.

Further, by injecting a contrast agent into the subject and imaging, it is possible to generate a contrast enhanced image in which a site with the contrast agent injected is enhanced. For example, by injecting a contrast agent into the subject and imaging by Contrast Harmonic Imaging (CHI), it is possible to generate a harmonic image based on harmonic waves. Then, a body tissue image representing the morphology of body tissue and a contrast enhanced image obtained in contrast imaging are simultaneously displayed. A body tissue image shows, for example, the morphology of tumor. Moreover, a contrast enhanced image shows a site with microbubbles of a contrast agent injected is enhanced. Even in the case of thus simultaneously displaying a body tissue image and a contrast enhanced image, it is difficult for the operator to grasp the positional relation between the tumor shown in the body tissue image and the site with the contrast agent injected shown in the contrast enhanced image. Therefore, it is difficult for the operator to determine whether or not the contrast agent is injected in the tumor based on the body tissue image and the contrast enhanced image. Besides, a method of displaying the contrast enhanced image and the body tissue image in the superimposed state is known, but there is a problem that contrast resolution (gradation) decreases because the two images are superimposed on each other.

Additionally, when the contrast enhanced image is superimposed on the body tissue image, the body tissue image is hidden behind the contrast enhanced image. Therefore, it is difficult for the operator to grasp the accurate positional relation between the site with the contrast enhanced image injected and the tissue shown in the body tissue image.

As described above, it is difficult for the operator to grasp the image positional relation between the body tissue image and the contrast enhanced image. Therefore, it is difficult to move the measurement caliper to the corresponding positions on the body tissue image and the contrast enhanced image to designate the measurement targets.

Further, the abovementioned method described in Japanese Examined Patent Publication No. 62-4978 is a method of executing the measurement on the image with the measurement caliper displayed of the B-mode image and the M-mode image. Therefore, it is difficult for the operator to execute the measurement by moving the measurement caliper to the corresponding positions on the plurality of ultrasound images. Besides, in the method described in Japanese Unexamined Patent Publication No. 11-221216, the measurement using the measurement caliper is not executed. Therefore, it is difficult to execute the measurement in the corresponding positions on the plurality of ultrasound images.

SUMMARY OF THE INVENTION

An object of the present invention is to provide an ultrasound imaging apparatus that can, in the case of simultaneously displaying a plurality of ultrasound images, specify positions corresponding to each other on the plurality of ultrasound images and measure measurement targets in the corresponding positions, and also provide a method for displaying an ultrasound image.

A first aspect of the present invention is an ultrasound imaging apparatus, comprising: an imaging part configured to acquire a plurality of ultrasound image data by sequentially imaging a subject with ultrasound waves; and a display controller configured to cause a display to display, side by side, a plurality of ultrasound images based on the plurality of ultrasound image data acquired by the imaging part and also cause the display to display measurement markers for obtaining quantitative information of tissues shown in the ultrasound images in a state superimposed on the plurality of ultrasound images in relatively same positions.

According to the first aspect, by displaying a plurality of ultrasound images side by side and displaying measurement markers in a state superimposed on the plurality of ultrasound images in relatively same positions, it is possible to easily specify positions corresponding to each other on the plurality of ultrasound images. Consequently, it is possible to measure measurement targets in the corresponding positions on the plurality of ultrasound images.

Further, a second aspect of the present invention is a method for displaying an ultrasound image, comprising: acquiring a plurality of ultrasound image data by sequentially imaging a subject with ultrasound waves; and displaying, side by side, a plurality of ultrasound images based on the plurality of ultrasound image data having been acquired, and also displaying measurement markers for obtaining quantitative information of tissues shown in the ultrasound images in a state superimposed on the plurality of ultrasound images in relatively same positions.

DETAILED DESCRIPTION OF THE EMBODIMENTS

Figure 1:
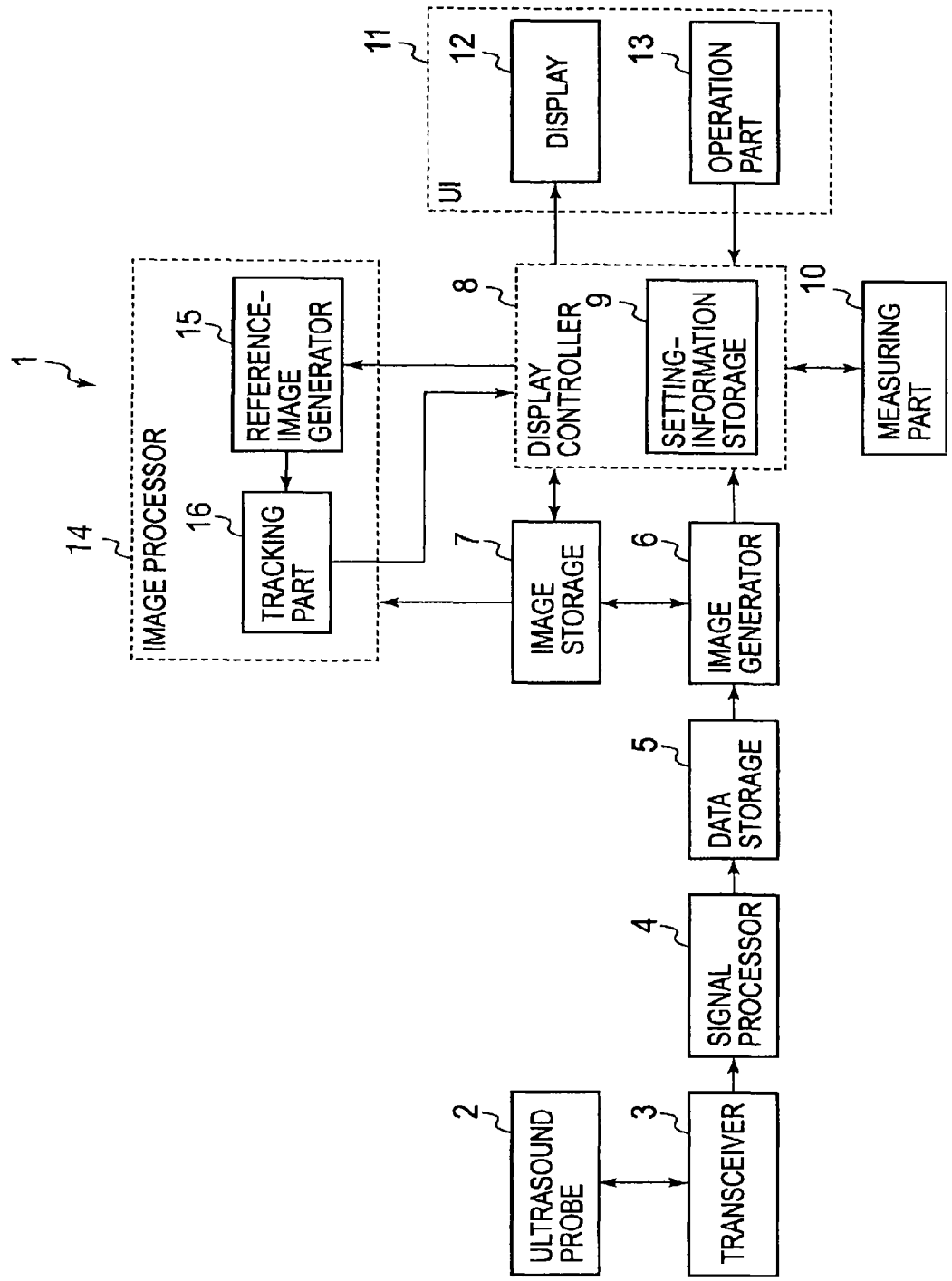
FIG. 1 is a block diagram showing an ultrasound imaging apparatus according to an embodiment of the present invention.

An ultrasound imaging apparatus according to an embodiment of the present invention will be described with reference to FIG. 1. FIG. 1 is a block diagram showing the ultrasound imaging apparatus according to the embodiment of the present invention.

An ultrasound imaging apparatus 1 according to this embodiment includes an ultrasound probe 2, a transceiver 3, a signal processor 4, a data storage 5, an image generator 6, an image storage 7, a display controller 8, a measuring part 10, a user interface (UI) 11, and an image processor 14.

As the ultrasound probe 2, a 1D array probe in which a plurality of ultrasound transducers are aligned in a scanning direction, or a 2D array probe in which a plurality of ultrasound transducers are two-dimensionally arranged is used. Alternatively, a mechanical 1D array probe capable of scanning a three-dimensional region by mechanically oscillating ultrasound transducers in a direction (an oscillating direction) orthogonal to the scanning direction may be used as the ultrasound probe 2.

The transceiver 3 includes a transmitter and a receiver. The transceiver 3 supplies electric signals to the ultrasound probe 2 to make the ultrasound probe 2 generate ultrasound waves, and receives echo signals received by the ultrasound probe 2.

The transmitter of the transceiver 3 includes a clock generation circuit, a transmission delay circuit, and a pulsar circuit, which are not shown in the drawings. The clock generation circuit generates clock signals that determine the transmission timing and transmission frequency of ultrasound signals. The transmission delay circuit executes transmission focus by applying a delay at the time of transmission of ultrasound waves. The pulsar circuit has a corresponding number of pulsars to the number of individual channels for the respective ultrasound transducers. The pulsar circuit generates a driving pulse at the delayed transmission timing and supplies an electric signal to each of the ultrasound transducers of the ultrasound probe 2.

Further, the receiver of the transceiver 3 includes a preamplifier circuit, an A/D conversion circuit, a reception delay circuit, and an adder circuit. The preamplifier circuit amplifies, for each reception channel, the echo signals outputted from the respective ultrasound transducers of the ultrasound probe 2. The A/D conversion circuit executes A/D conversion on the amplified echo signals. The reception delay circuit applies a delay time necessary for determining the reception directionality to the echo signals after the A/D conversion. The adder circuit adds the echo signals to which the delay time has been applied. By the adding, reflection components from a direction corresponding to the reception directionality are enhanced. The signals added by the transceiver 3 will be referred to as "RF data."

The signal processor 4 includes a B-mode processor. The B-mode processor visualizes echo amplitude information and generates B-mode ultrasound raster data from the echo signals. To be specific, the B-mode processor executes the Band Pass Filter process on reception signals sent from the transceiver 3, and thereafter, detects the envelope of output signals.

Then, the B-mode processor executes the compression process by logarithmic transformation on the detected data, thereby visualizing the echo amplitude information.

Further, the signal processor 4 may include a Doppler processor. The Doppler processor, for example, executes quadrature detection on reception signals sent from the transceiver 3 to derive Doppler shift frequency components, and executes the FFT (Fast Fourier Transform) process to generate a Doppler frequency distribution representing the blood-flow rate.

Furthermore, the signal processor 4 may include a CFM (Color Flow Mapping) processor. The CFM processor visualizes blood-flow information, and generates color ultrasound raster data. The blood-flow information includes information such as velocity, distribution and power, and the blood-flow information is obtained as binary information.

The reception signals outputted from the transceiver 3 are processed by any processor. The signal processor 4 outputs the ultrasound raster data after the signal processing to the data storage 5.

The data storage 5 is composed of a storage device such as a memory and a hard disk drive. The data storage 5 stores the ultrasound raster data generated by the signal processor 4.

The image generator 6 reads the ultrasound raster data after the signal processing from the data storage 5, and converts the data after the signal processing to coordinate data based on the spatial coordinate system (digital scan conversion). For example, the image generator 6 executes the scan conversion process on the data after the signal processing outputted from the B-mode processor, thereby generating B-mode image data representing the morphology of tissue of the inside of the subject. As an example, scan of a two-dimensional cross section (a scan plane) with ultrasound waves is executed by the ultrasound probe 2 and the transceiver 3, and the image generator 6 generates B-mode image data (referred to as "tomographic image data" hereinafter) that two-dimensionally represents the morphology of tissue in the cross section. The image generator 6 outputs the tomographic image data to the image storage 7 and the display controller 8.

The image storage 7 is composed of a storage device such as a memory and a hard disk, and stores the tomographic image data generated by the image generator 6. Moreover, the image storage 7 attaches a time when each of the tomographic image data has been acquired as attached information to each tomographic data and stores each of the tomographic image data.

Moreover, in the case of acquiring an ECG (Electrocardiogram) waveform of the subject by using an electrocardiograph (not shown), a controller (not shown) receives the ECG waveform from outside the ultrasound imaging apparatus 1. Then, the not-shown controller causes the image storage 7 to store tomographic image data so as to be associated with a time phase received at the timing of acquisition of the tomographic image data.

The display controller 8 receives the tomographic image data outputted from the image generator 8 and causes a display 12 to display a tomographic image based on the tomographic image data. Moreover, the display controller 8 reads the tomographic image data stored in the image storage 7 and causes the display 12 to display a tomographic image based on the tomographic image data.

The user interface (UI) 11 includes the display 12 and an operation part 13. The display 12 is composed of a monitor such as a CRT and a liquid crystal display. On the screen of the display 12, an ultrasound image such as a tomographic image and a three-dimensional image is displayed. The operation part 13 is composed of a pointing device such as a mouse and a trackball, a switch, various buttons, a keyboard, or a TCS (Touch Command Screen).

The ultrasound probe 2, the transceiver 3, the signal processor 4 and the image generator 6 compose an example of an "imaging part" of the present invention. Moreover, the image storage 7 is equivalent to an example of an "image storage" of the present invention. Moreover, the display controller 8 is equivalent to an example of a "display controller" of the present invention. Moreover, the operation part 13 is equivalent to an example of an "operation part" of the present invention.

Further, volume scan may be executed by the ultrasound probe 2 and the transceiver 3. In this case, the signal processor 4 outputs volume data acquired in the volume scan to the data storage 5, and the data storage 5 stores the volume data. The image generator 6 reads the volume data from the data storage 5 and executes volume rendering on the volume data, thereby generating three-dimensional image data that three-dimensionally represents tissue of the inside of the subject. Alternatively, the image generator 6 may execute the MPR (Multi Planar Reconstruction) process on the volume data, thereby generating image data (MPR image data) in an arbitrary cross section.

(Display of a Plurality of Images)

In this embodiment, the display controller 8 causes the display 12 to simultaneously display, side by side, a plurality of tomographic images based on a plurality of tomographic image data. For example, sequential scan of one cross section of the subject is executed by the ultrasound probe 2 and the transceiver 3, and the image generator 6 sequentially generates tomographic image data in the cross section. Then, when the operator designates a desired time phase by using the operation part 13, the display controller 8 reads tomographic image data acquired in the designated time phase from the image storage 7 and causes the display 12 to display a tomographic image based on the tomographic image data. As an example, when the operator designates two desired time phases by using the operation part 13, the display controller 8 reads two tomographic image data acquired in the two designated time phases from the image storage 7, and causes the display 12 to simultaneously display two tomographic images side by side. For example, when receiving an instruction for displaying a plurality of images from the operation part 13, the display controller 8 splits the screen of the display 12 into a plurality of regions, and causes each of the split regions to display a tomographic image.

As an example, in the case of displaying two images side by side, the display controller 8 splits the screen of the display 12 into two regions. Then, the display controller 8 causes the display 12 to display a tomographic image in each of the split regions.

Figure 2:
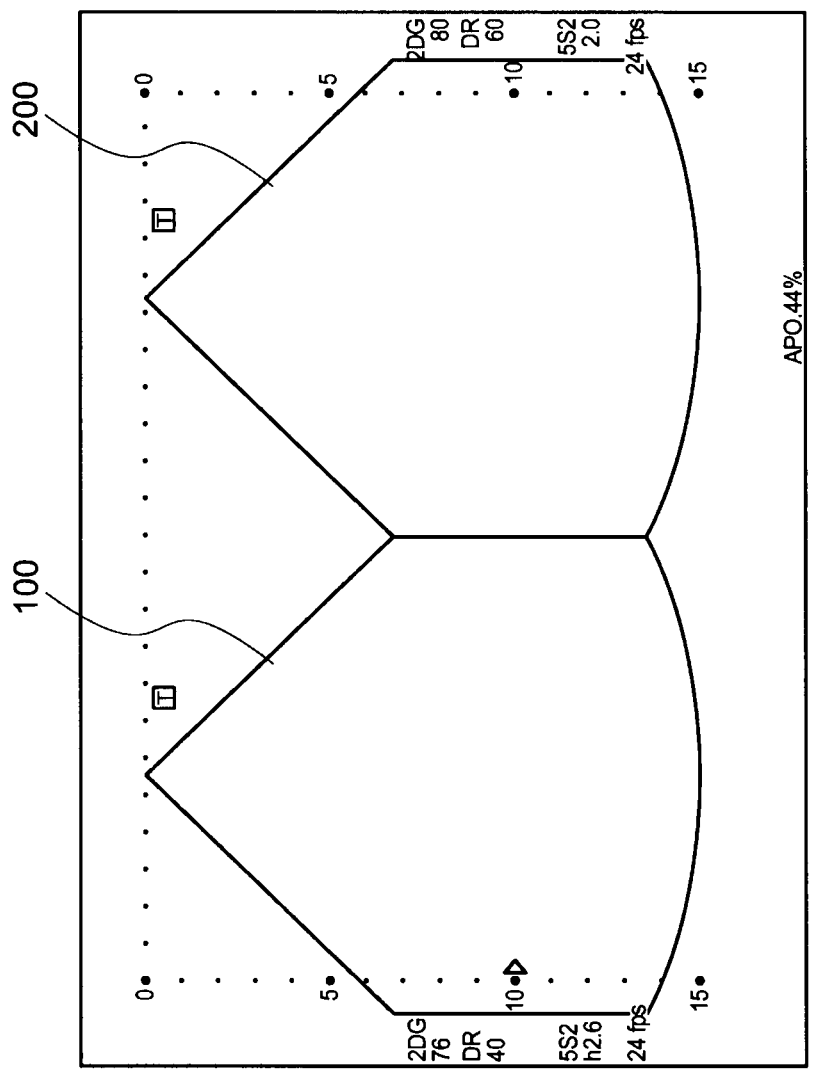
FIG. 2 is a view showing an example of a screen displaying two tomographic images side by side.

Here, an example of an ultrasound image displayed on the display 12 will be shown in FIG. 2. FIG. 2 is a view showing an example of a screen displaying two tomographic images side by side. As shown in FIG. 2, the display controller 8 causes the display 12 to simultaneously display a tomographic image 100 and a tomographic image 200 side by side. For example, the tomographic image 100 and the tomographic image 200 are images generated by scanning one cross section of the subject and acquired at different times.

(Contrast Imaging)

Further, a plurality of ultrasound images captured in a state that a contrast agent is injected in the subject may be simultaneously displayed side by side. For example, in a state that a contrast agent is injected in the subject, the inside of the subject is scanned by the ultrasound probe 2 and the transceiver 3. Then, the image generator 6 generates harmonic image data based on harmonic components of the reception signals by the Contrast Harmonic Imaging (CHI) method. Besides, the image generator 6 generates body tissue image data representing body tissue based on fundamental components of the reception signals. A harmonic image shows a site in which microbubbles of the contrast agent are injected is enhanced. On the other hand, a body tissue image shows the morphology of each site, the morphology of a lesion site such as tumor, or the like. Then, sequential scan of one cross section of the subject is executed by the ultrasound probe 2 and the transceiver 3, and the image generator 6 sequentially generates the body tissue image data and the harmonic image data in the cross section. The body tissue image data and the harmonic image data generated by the image generator 6 are stored into the image storage 7. The display controller 8 receives the body tissue image data and the harmonic image data outputted from the image generator 6, and causes the display 12 to simultaneously display, side by side, a body tissue image based on the body tissue image data and a harmonic image based on the harmonic image data. Moreover, when the operator designates a desired time phase by using the operation part 13, the display controller 8 reads, from the image storage 7, the body tissue image data and the harmonic image data acquired in the designated time phase, and causes the display 12 to simultaneously display the body tissue image and the harmonic image side by side. The harmonic image data is equivalent to an example of "contrast-agent image data" of the present invention.

(Measurement Marker)

The display controller 8 causes the display 12 to display a measurement marker (a measurement caliper) on an ultrasound image. This measurement marker is used for obtaining quantitative information of tissue shown in an ultrasound image. Plural types of measurement markers are prepared depending on the intended use of measurement, and data representing a measurement marker having an initial shape and an initial size is previously stored in a setting-information storage 9. For example, a measurement marker for measuring the distance between two points, a measurement marker for measuring the perimeter of a site, a measurement marker for measuring the area of a site, etc. are prepared. Data representing these measurement markers are previously stored in the setting-information storage 9.

The display controller 8 causes the display 12 to display the measurement markers in a state superimposed on a plurality of ultrasound images in relatively the same positions. By operating the operation part 13, the operator can move the measurement marker to a desired position on the screen of the display 12. For example, when the operator moves the mouse or the trackball, the display controller 8 receives information representing the movement amount thereof from the operation part 13 and controls to display the measurement marker in a position according to the movement amount on the screen of the display 12.

Here, as an example, a measurement marker for measuring the distance between two points will be described with reference to FIGS. 3 through 10. FIGS. 3 through 10 are views showing an example of a screen displaying the measurement marker on a screen displaying two tomographic images side by side.

Figure 3:
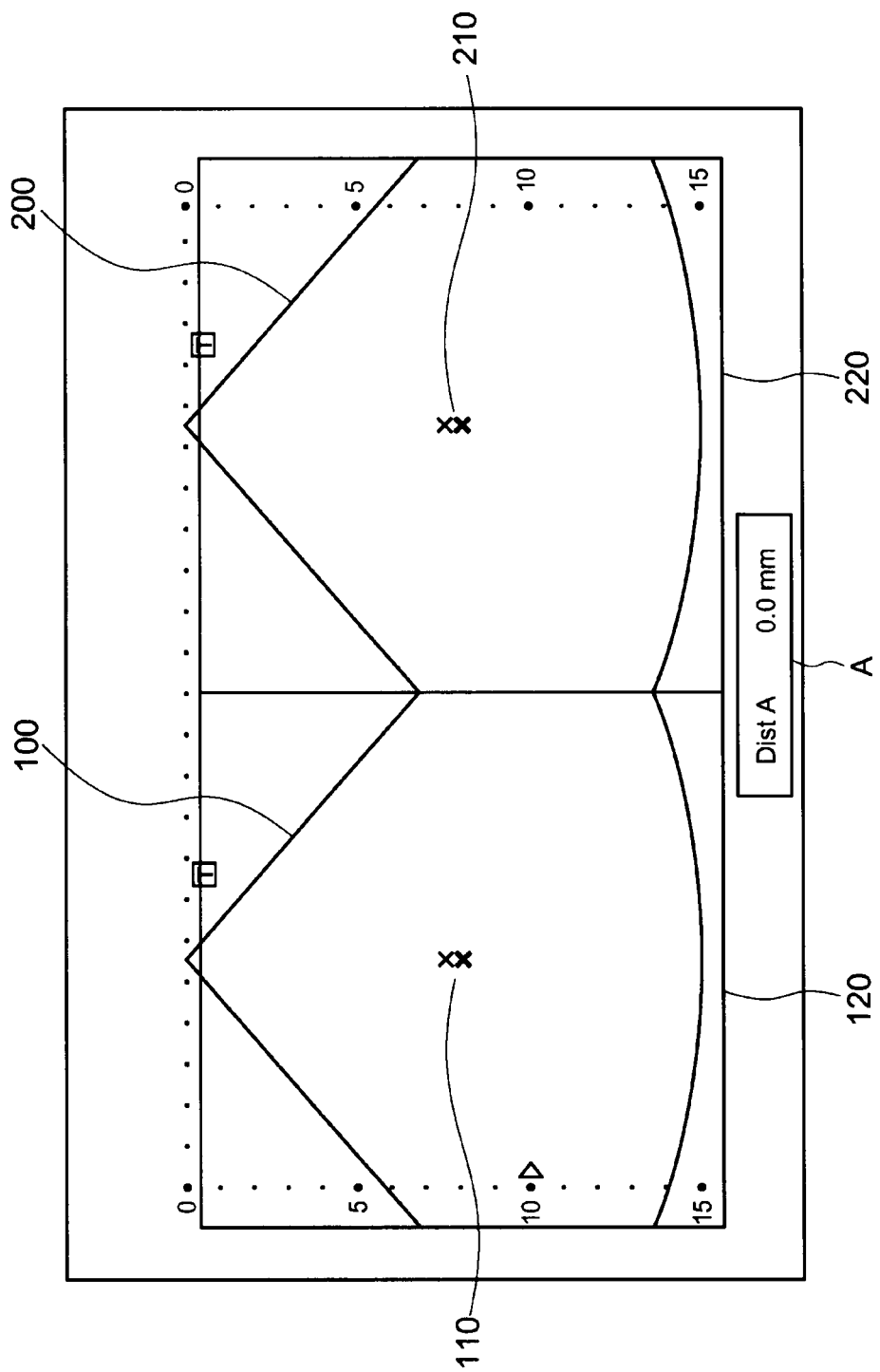
FIG. 3 is a view showing an example of a screen displaying measurement markers on a screen displaying two tomographic images side by side.

The display controller 8 reads data representing the measurement marker of an initial state from the setting-information storage 9 and controls to display the measurement marker in an initial position on the screen of the display 12. For example, as shown in FIG. 3, the display controller 8 splits a region on the screen of the display 12 into a first display region 120 and a second display region 220. Then, the display controller 8 controls to display the tomographic image 100 within the first display region 120 and controls to display the tomographic image 200 within the second display region 220.

Besides, the display controller 8 controls to display a first measurement marker 110 in the middle of the first display region 120 for displaying the tomographic image 100. The display controller 8 also controls to display a second measurement marker 210 in the middle of the second display region 220 for displaying the tomographic image 200. The first display region 120 is a range in which the first measurement marker 110 can move, and the second display region 220 is a range in which the second measurement marker 210 can move. As an example, each of the first measurement marker 110 and the second measurement marker 210 is composed of a major marker (a major caliper) and a minor marker (a minor caliper), which have cross shapes. The major marker is a marker for designating the start point of the two points, and the minor marker is a marker for designating the end point.

Then, by using the operation part 13, the operator designates either the first measurement marker 110 or the second measurement marker 210 and moves the designated measurement marker. For example, the operator designates the first measurement marker 110 by using the operation part 13 and moves the first measurement marker 110. The display controller 8 receives information representing the movement amount from the operation part 13 and controls to display the first measurement marker 110 in a position according to the movement amount within the first display region 120. It is preferred that the display controller 8 causes the display 12 to display a measurement marker designated by the operator so as to be distinguishable from the other measurement marker. For example, it is preferred that the display controller 8 causes the display 12 to display a measurement marker designated by the operator with color or size different from that of the other measurement marker. In the example shown in FIG. 3, the display controller 8 can cause the display 12 to display the first measurement marker 110 with color or size different from that of the second measurement marker 210.

Consequently, the operator can recognize a measurement marker to be operated and can recognize an image on which the measurement marker to be operated is displayed.

Figure 4:
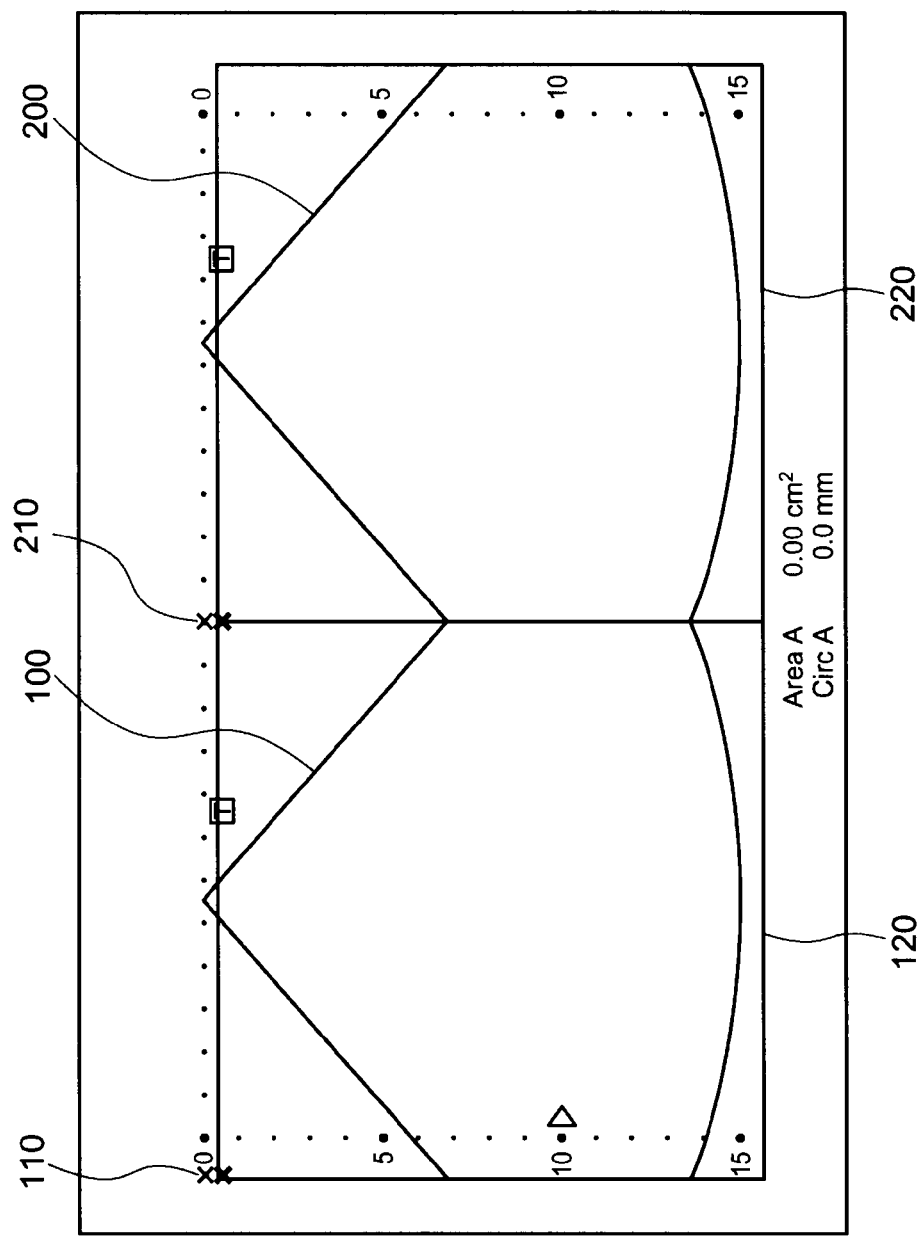
FIG. 4 is a view showing an example of a screen displaying measurement markers on a screen displaying two tomographic images side by side.

Furthermore, the display controller 8 controls to display the second measurement marker 210 in relatively the same position as the first measurement marker 110 within the second display region 220. For example, as shown in FIG. 4, the display controller 8 controls to display the first measurement marker 110 and the second measurement marker 210 in relatively the same positions within the first display region 120 and the second display region 220, respectively.

For example, with reference to the coordinate system on the screen of the display 12, the display controller 8 controls to display the first measurement marker 110 and the second measurement marker 120 in relatively the same positions within the first display region 120 and the second display region 220, respectively. That is, the display controller 8 specifies the position of the first measurement marker 110 within the first display region 120 and controls to display the second measurement marker 210 in relatively the same position as the specified position, within the second display region 220.

Alternatively, with reference to the coordinate system on the real space in which the tomographic image 100 and the tomographic image 200 have been acquired, the display controller 8 may control to display the first measurement marker 110 and the second measurement marker 210, respectively, in relatively the same positions on the real space within the first display region 120 and the second display region 220. That is, the display controller 8 specifies the position on the real space of the first measurement marker 110 on the tomographic image I 00 and controls to display the second measurement marker 210 in a position on the tomographic image 200 corresponding to a position on the real space that is relatively the same as the position on the real space of the first measurement marker 110.

For example, the display controller 8 specifies the position on the real space of the first measurement marker 110 in accordance with the movement amount outputted from the operation part 13. Besides, the display controller 8 specifies, in the split region on the screen, a position corresponding to the position on the real space of the first measurement marker 110 and controls to display the first measurement marker 110 in the specified position. In other words, the display controller 8 specifies, within the first display region 120, a position corresponding to the position on the real space of the first measurement marker 110 and controls to display the first measurement marker 110 in the specified position. In addition, the display controller 8 controls to display, within the second display region 220, the second measurement marker 210 in a position that is relatively the same as the position on the real space of the first measurement marker 110.

To be specific, the display controller 8 controls to display the first measurement marker 110 and the second measurement marker 210 on the tomographic image 100 and the tomographic image 200, in equal positions (depths) in the depth direction and equal positions in the scanning direction.

By thus displaying the measurement markers with reference to the coordinate system on the real space, even if conditions such as the depth of transmission of ultrasound waves, the width of scan and the magnification of an image are different among a plurality of ultrasound images, it is possible to display the measurement markers in relatively the same positions on the plurality of ultrasound images. For example, even if the size and magnification of an image, etc. are different between the tomographic image 100 and the tomographic image 200, it is possible to display the measurement markers in relatively the same positions on the tomographic image 100 and the tomographic image 200 by displaying the measurement markers with reference to the coordinate system on the real space.

Figure 5:
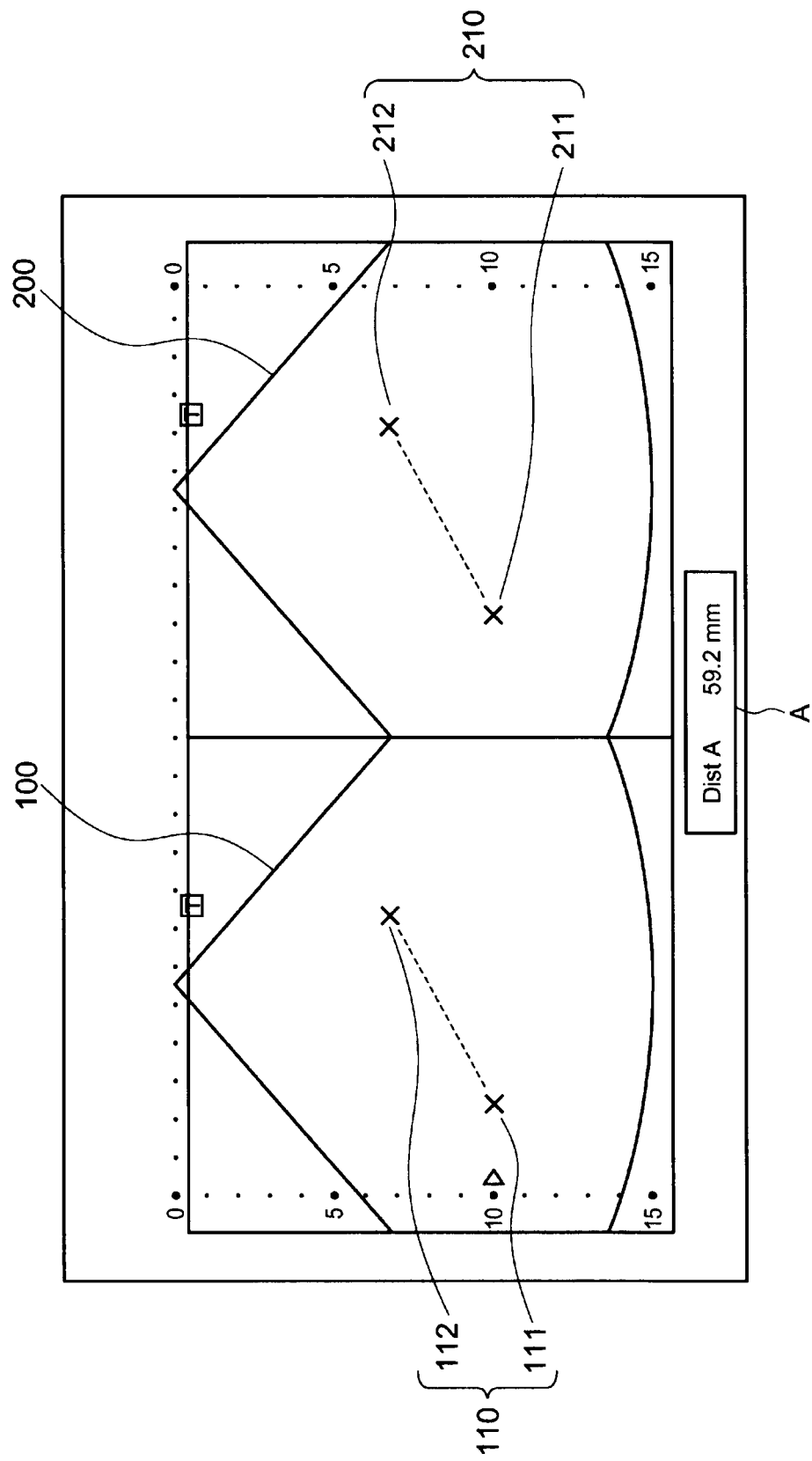
FIG. 5 is a view showing an example of a screen displaying measurement markers on a screen displaying two tomographic images side by side.

Then, the operator moves the first measurement marker 110 to a desired position by using the operation part 13 and fixes the position of a first major marker 111 constituting the first measurement marker 110. For example, as shown in FIG. 5, the display controller 8 moves the first major marker 111 constituting the first measurement marker 110 to the designated position in accordance with the movement amount outputted from the operation part 13, and controls to display it on the display 12. Then, the display controller 8 fixes the first major marker 111 in a position of the movement destination in accordance with the instruction for fixing the position by the operation part 13, and controls to display it on the display 12. Besides, the display controller 8 fixes, within the second display region 220, a second major marker 211 constituting the second measurement marker 210 in relatively the same position as the first major marker 111, and controls to display the second major marker 211.

At this point, it is possible to freely move a first minor marker 112 constituting the first measurement marker 110 and a second minor marker 212 constituting the second measurement marker 210. The operator moves the first minor marker 112 constituting the first measurement marker 110 to a desired position by using the operation part 13. In accordance with the movement amount outputted from the operation part 13, the display controller 8 moves the first minor marker 112 to a designated position and controls to display it on the display 12. At this moment, the display controller 8 controls to display the second minor marker 212 constituting the second measurement marker 210 in relatively the same position as that of the first minor marker 112 within the second display region.

Coordinate information representing the position of the first major marker and coordinate information representing the position of the first minor marker are outputted from the display controller 8 to the measuring part 10.

For example, coordinate information representing the position on the real space of the first major marker and coordinate information representing the position of the first minor marker are outputted from the display controller 8 to the measuring part 10.

(Measuring Part 10)

The measuring part 10 obtains quantitative information of tissue designated by the measurement marker. In the case of obtaining the distance between two points, the measuring part 10 receives, from the display controller 8, coordinate information representing the position on the real space of the first major marker 111 and coordinate information representing the position of the first minor marker 112, and obtains the distance between the first major marker 111 and the first minor marker 112. For example, the measuring part 10 obtains the length of a line between the first major marker 111 and the first minor marker 112. Alternatively, the measuring part 10 may obtain the length of a curve between the first major marker 111 and the first minor marker 112. In the case of obtaining the length of the curve, the measuring part 10, for example, sets a spline curve between the first major marker 111 and the first minor marker 112 and obtains the length of the spline curve. Then, the measuring part 10 outputs the measurement value to the display controller 8. For example, the measuring part 10 outputs, to the display controller 8, information representing the length of a line between the first major marker 111 and the first minor marker 112. The display controller 8 receives the measurement value from the measuring part 10 and controls to display the measurement value on the display 12. For example, as shown in FIG. 5, the display controller 8 controls to display the measurement value in a display field A. Since the distance between two points is measured as an example, the distance between the first major marker 111 and the first minor marker 112 is displayed as the measurement value (Dist A: 59.2 mm) on the display 12. The measuring part 10 is equivalent to an example of a "measuring part" of the present invention.

Further, by using the operation part 13, the operator can move the first minor marker 112 and the second minor marker 212 to desired positions. The measuring part 10 receives coordinate information representing the movement destination position of the first minor marker 112 from the display controller 8 and newly obtains the distance between the first major marker 111 and the first minor marker 112. The display controller 8 controls to display the newly obtained distance between the two points on the display 12. Thus, as the first minor marker 112 (the second minor marker 212) is moved, the measuring part 10 newly obtains the distance between the first major marker 111 and the first minor marker 112, and the display controller 8 controls to display the new distance on the display 12.

The second major marker 211 constituting the second measurement marker 210 is displayed in the same position on the real space as the first major marker 111. Moreover, the second minor marker 212 constituting the second measurement marker 210 is displayed in the same position on the real space as the first minor marker 112. Consequently, the distance between the second major marker and the second minor marker is equal to the distance between the first major marker and the first minor marker. Therefore, the measuring part 10 can receive, from the display controller 8, either the coordinate information of the first measuring marker 110 or the coordinate information of the second measuring marker 210, thereby obtaining the distance between two points.

Then, the operator fixes the position of the first minor marker 112 constituting the first measurement marker 110 by using the operation part 13.

Figure 6:
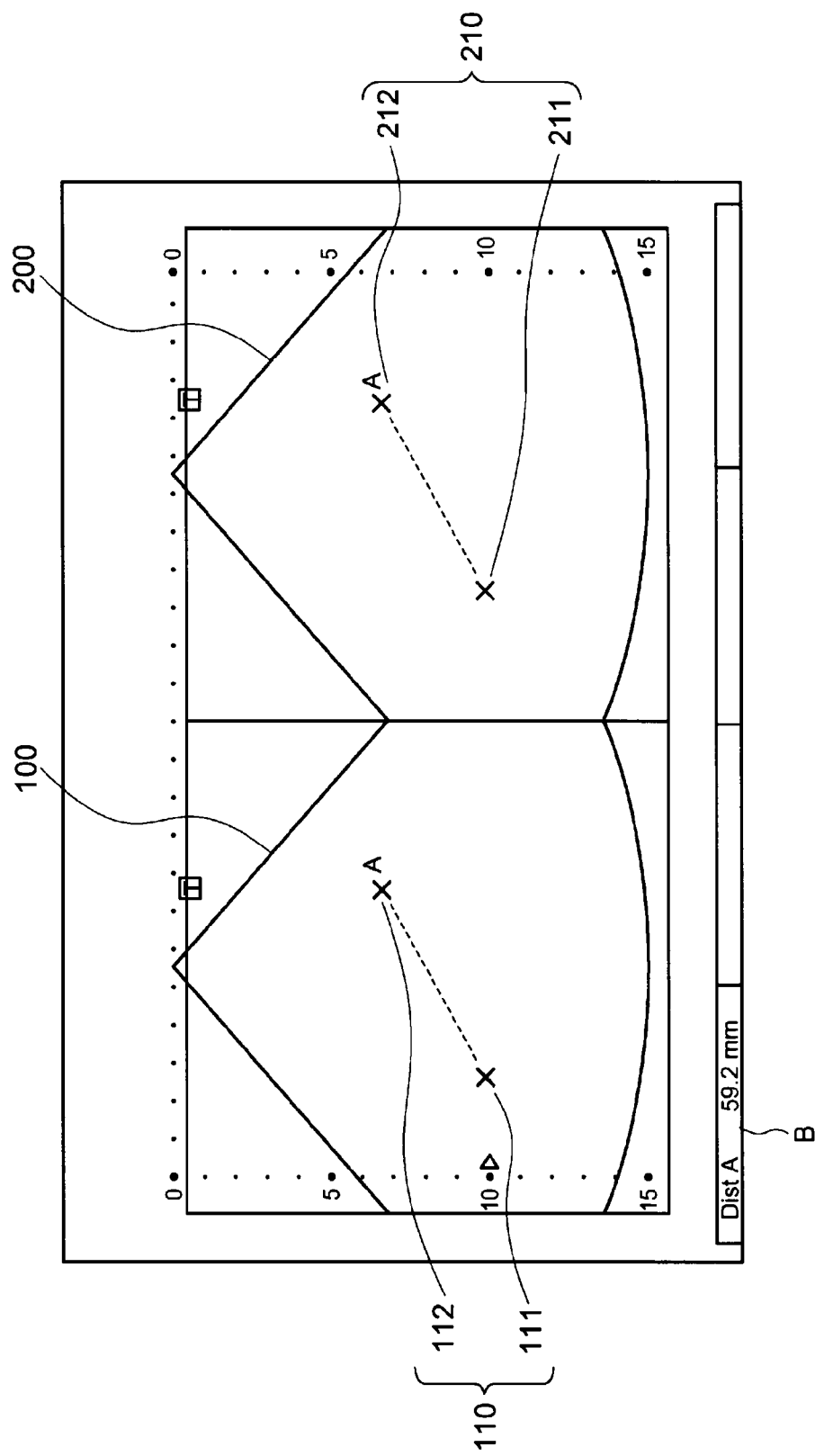
FIG. 6 is a view showing an example of a screen displaying measurement markers on a screen displaying two tomographic images side by side.

In accordance with the instruction for fixing the position by the operation part 13, the display controller 8 fixes the first minor marker 112 and the second minor marker 212 in the movement destination positions and controls to display on the display 12. Then, the display controller 8 controls to display the measurement value obtained by the measuring part 10 in a display field B as shown in FIG. 6.

The display controller 8 may generate a linear marker connecting the major marker and the minor marker and cause the display 12 to display the linear marker between the major marker and the minor marker. For example, as shown in FIGS. 5 and 6, the display controller 8 controls to display a linear marker connecting the first major marker 111 and the first minor marker 112 between the first major marker 111 and the first minor marker 112. The display controller 8 also controls to display a linear marker connecting the second major marker 211 and the second minor marker 212 between the second major marker 211 and the second minor marker 212.

Alternatively, it is possible to configure to rotate a measurement marker. When the operator designates a measurement marker and gives an instruction for rotating by using the operation part 13, the display controller 8, in accordance with the instruction for rotating, rotates the measurement marker about a predetermined axis and controls to display on the display 12.

Figure 7:
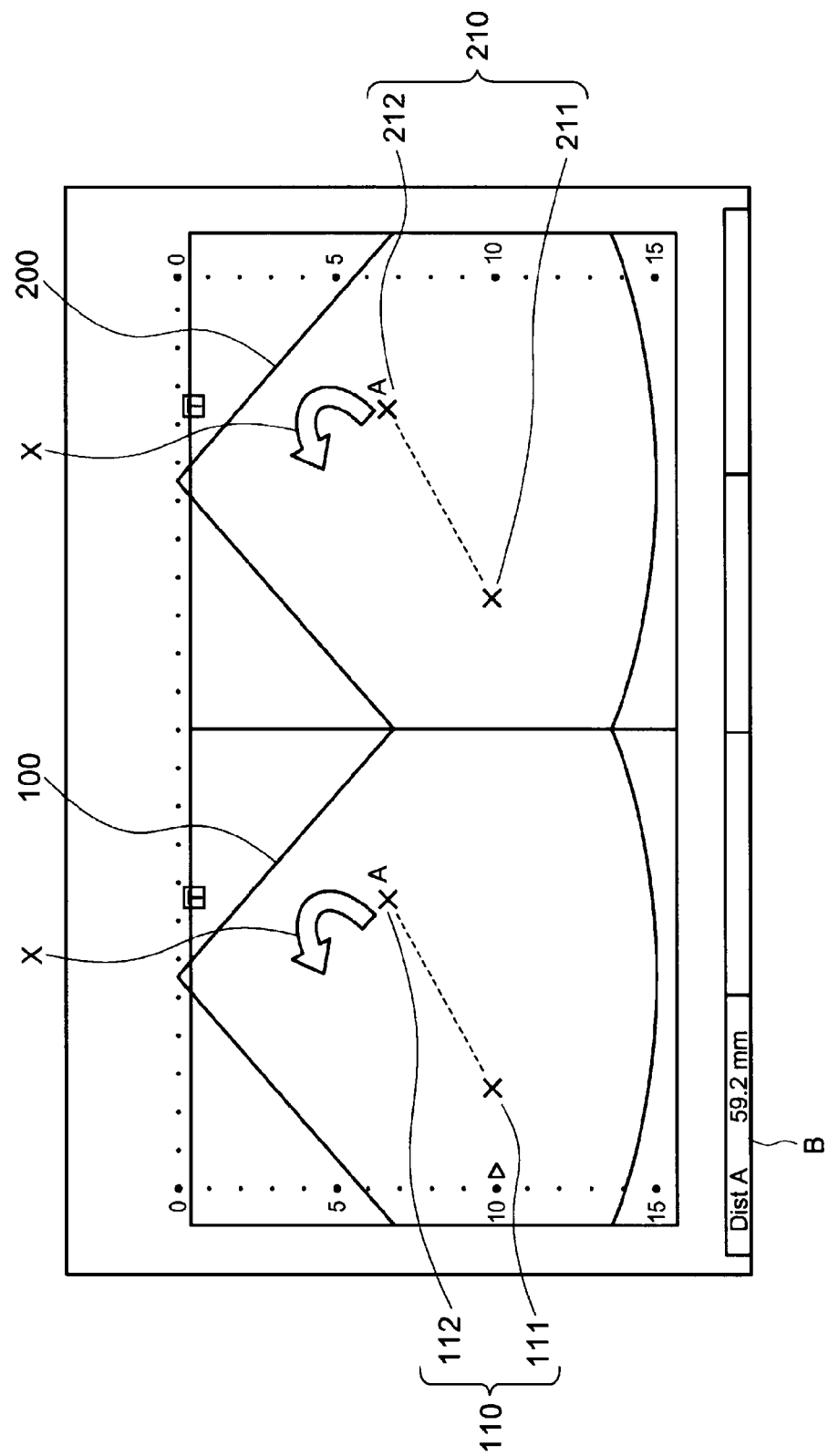
FIG. 7 is a view showing an example of a screen displaying measurement markers on a screen displaying two tomographic images side by side.

For example, the operator designates the first measurement marker 110 by using the operation part 13, and rotates the first measurement marker 110 in the X direction as shown in FIG. 7. In accordance with the rotation amount outputted from the operation part 13, the display controller 8 rotates the first measurement marker 110 in the X direction and controls to display on the display 12. At this moment, in accordance with the rotation amount, the display controller 8 rotates the second measurement marker 210 in the X direction in the same manner as the first measurement marker 110 and controls to display on the display 12. When the measurement marker is thus rotated and a new position is designated, coordinate information representing the position of the first major marker 111 and coordinate information representing the position of the first minor marker 112 after rotation are outputted to the measuring part 10. The measuring part 10 obtains the distance between the first major marker 111 and the first minor marker 112 after rotation, and the display controller 8 controls to display the distance on the display 12.

Figure 8:
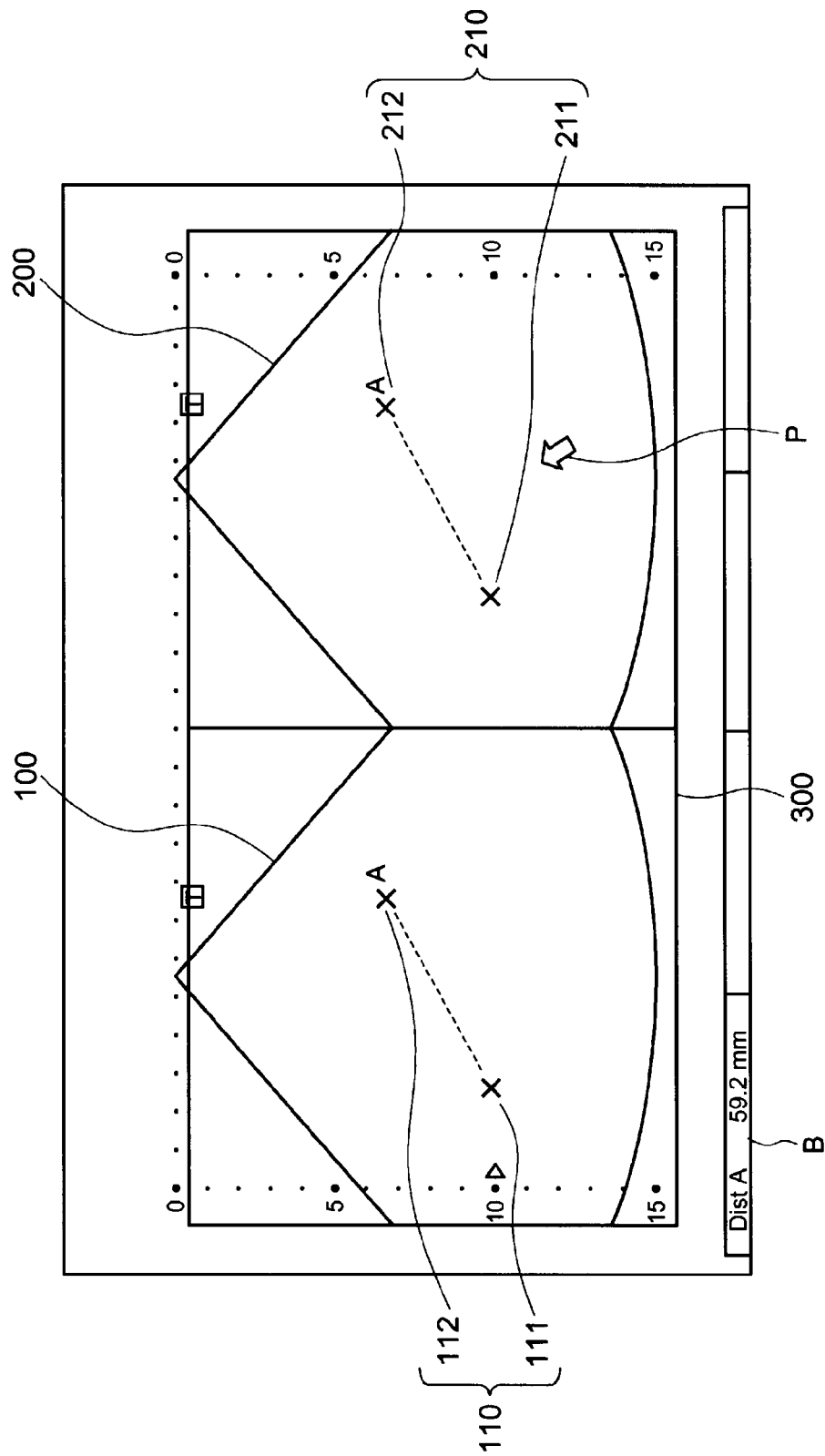
FIG. 8 is a view showing an example of a screen displaying measurement markers on a screen displaying two tomographic images side by side.

Further, it is possible to configure so that the position of the measurement marker can be corrected after the first measurement marker 110 and the second measurement marker 210 are fixed and displayed. In this case, when the operator instructs correction of the measurement marker by using the operation part 13, a signal representing the instruction is outputted to the display controller 8. The display controller 8 receives the instruction and causes the display 12 to display a cursor for designating the measurement marker to be corrected. Data representing this cursor is previously stored in the setting-information storage 9. For example, as shown in FIG. 8, the display controller 8 controls to display a cursor P within an image region 300 including the tomographic image 100 and the tomographic image 200. The cursor P can be moved within the image region 300.

Figure 9:
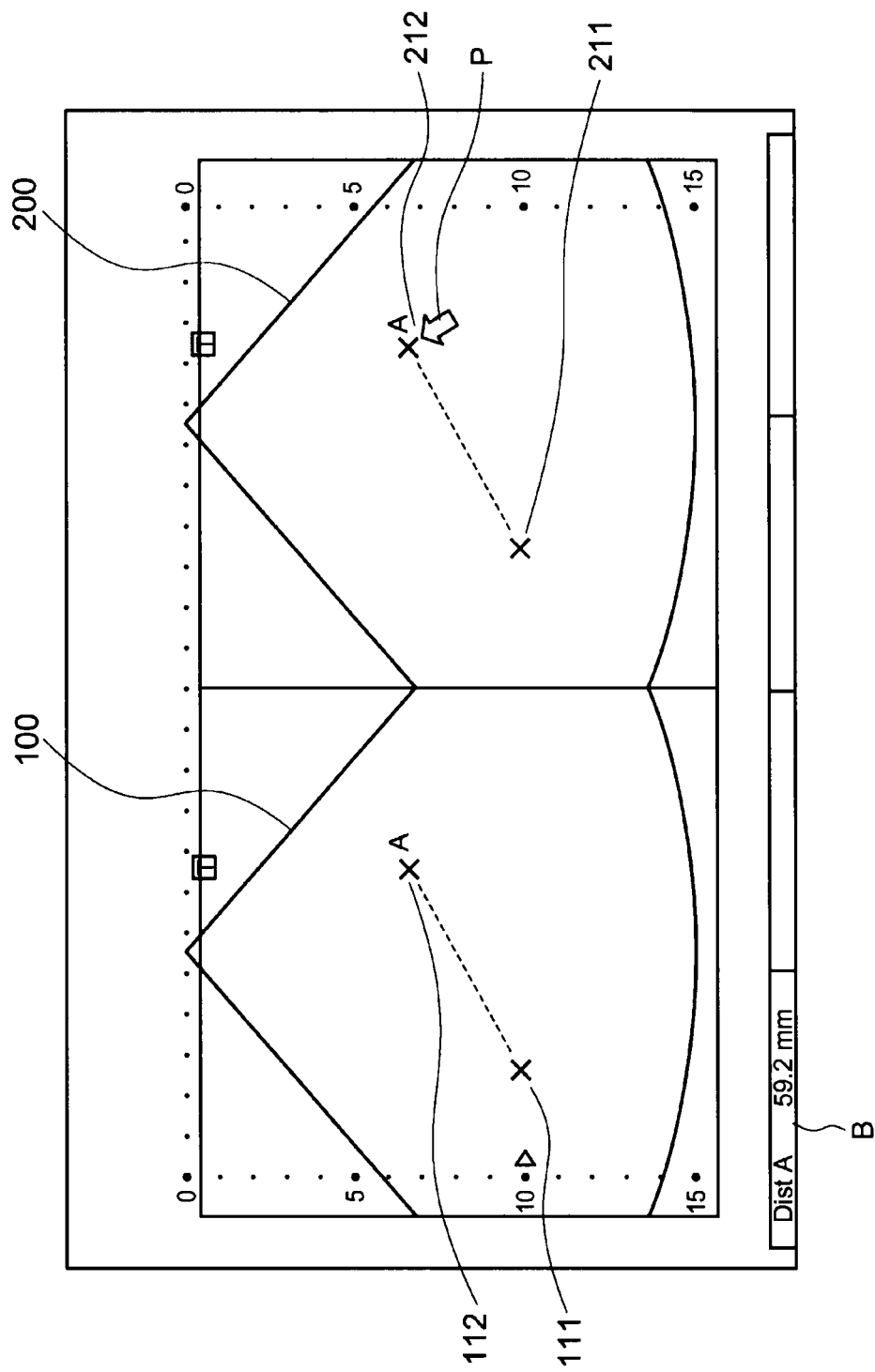
FIG. 9 is a view showing an example of a screen displaying measurement markers on a screen displaying two tomographic images side by side.

The operator moves the cursor P by using the operation part 13 and designates a marker whose position is to be changed. For example, as shown in FIG. 9, when the operator designates the second minor marker 212 with the cursor P by using the the operation part 13, the second minor marker 212 and the first minor marker 112 corresponding to the second minor marker 212 are set into the display controller 8 as movable markers. The display controller 8 causes the display 12 to display the second minor marker 212 designated with the cursor P so as to be distinguishable from the other markers. For example, the display controller 8 causes the display 12 to display the second minor marker 212 in different color from the other markers. By thus displaying a marker designated with the cursor P so as to be distinguishable from the other markers, it is possible to make the operator grasp a marker that is a correction target and is movable. Moreover, the display controller 8 may cause the display 12 to display the first minor marker 112 corresponding to the second minor marker 212 in different color.

Figure 10:
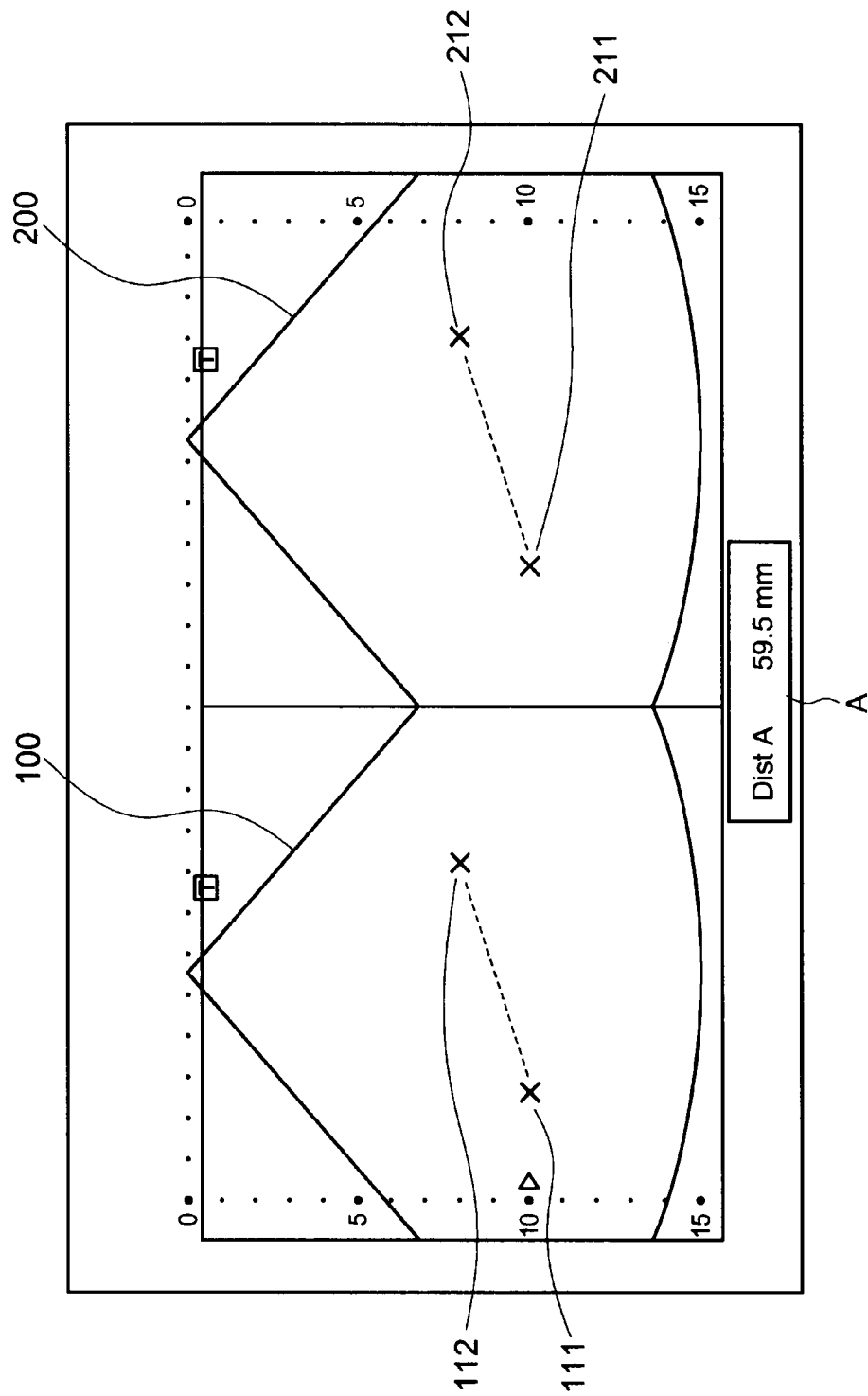
FIG. 10 is a view showing an example of a screen displaying measurement markers on a screen displaying two tomographic images side by side.

Then, as shown in FIG. 10, the operator moves the second minor marker 212 (the first minor marker 112) to a desired position by using the operation part 13. In accordance with the movement amount outputted from the operation part 13, the display controller 8 moves the second minor marker 212 to a designated position and controls to display on the display 12. At this moment, the display controller 8 controls to display the first minor marker 112 in relatively the same position as the second minor marker 212, within the first display region. When the position of the first measurement marker 110 (the second measurement marker 210) is newly designated in this manner, coordinate information representing the position of the first major marker 111 and coordinate information representing the position of the first minor marker 112 are outputted from the display controller 8 to the measuring part 10. The measuring part 10 newly obtains the distance between the first major marker 111 and the first minor marker 112, and the display controller 8 controls to display the distance as the measurement value in the display field A.

(Another Example of Measurement Marker)

Figure 11:
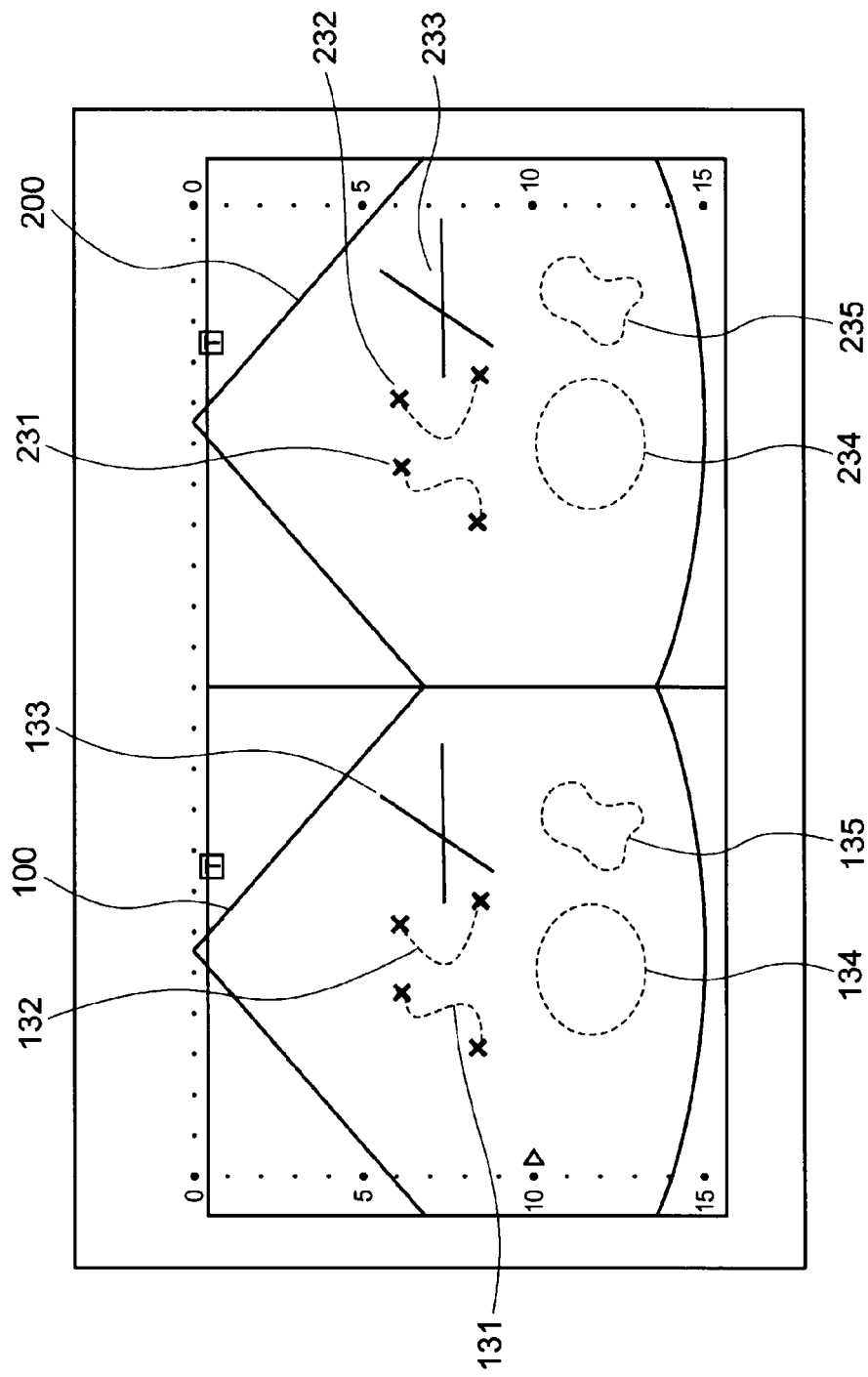
FIG. 11 is a view of a screen displaying an example of measurement markers.

Other than a measurement marker for measuring the distance between two points, various measurement markers may be used. For example, it is possible to use a measurement marker having a circular shape, an elliptical shape, a rectangular shape, a mesh shape, a triangular shape, or any curved shape. Measurement markers with initial shapes are previously stored in the setting-information storage 9 and, when the operator selects a desired measurement marker by using the operation part 13, the display controller 8 causes the display 12 to display the selected measurement marker. Besides, the measurement marker is configured so that the operator can arbitrarily change the size thereof other than the position thereof by using the operation part 13. Here, an example of the measurement marker will be described with reference to FIG. 11. FIG. 11 is a view of a screen showing an example of the measurement marker.

(Measurement Marker for Obtaining Angle

Fog example, the display controller 8 causes the display 12 to display a first measurement marker 133 and a second measurement marker 233, which are two linear markers crossing each other, in a state superimposed on the tomographic image 100 and the tomographic image 200, respectively. When the operator moves the first measurement marker 133 to a desired position on the tomographic image 100 by using the operation part 13, the display controller 8, in accordance with the movement amount outputted from the operation part 13, moves the first measurement marker 133 to a designated position and controls to display on the display 12. The display controller 8 controls to display the second measurement marker 233 in relatively the same position as the first measurement marker 133, on the tomographic image 200.

Moreover, when the operator changes the angle formed by the two markers composing the first measurement marker 133 by using the operation part 13, the display controller 8, in accordance with an angle designated by the operation part 13, changes the angle formed by the two markers composing the first measurement marker 133 and the angle formed by the two markers composing the second measurement marker 233, and controls to display on the display 12. The measuring part 10 receives coordinate information of the two linear markers composing the first measurement marker 133 from the display controller 8, and obtains an angle at which the two linear markers cross each other. The display controller 8 causes the display 12 to display the angle as the measurement value.

(Circular Measurement Marker)

Further, the display controller 8 may cause the display 12 to display a first measurement marker 134 and a second measurement marker 234, which have circular shapes, on the tomographic image 100 and the tomographic image 200, respectively. When the operator moves the first measurement marker 134 to a desired position on the tomographic image by using the operation part 13, the display controller 8, in accordance with the movement amount outputted from the operation part 13, moves the first measurement marker 134 to the designated position, and controls to display on the display 12. At this moment, the display controller 8 controls to display the second measurement marker 234 in relatively the same position as the first measurement marker 134 on the tomographic image 200. Moreover, when the operator changes the size of the first measurement marker 134 by using the operation part 13, the display controller 8, in accordance with the size designated by the operation part 13, changes the size of the first measurement marker 134 and the size of the second measurement marker 234, and controls to display on the display 12. The measuring part 10 receives coordinate information of the first measurement marker 134 from the display controller 8, and obtains the perimeter of a circle indicated by the first measurement marker 134 and the area of the inside of the circle. The display controller 8 causes the display 12 to display the perimeter and the area as the measurement values. For example, by surrounding a site to be measured with a circular measurement marker, it is possible to obtain the perimeter and area of the site.

(Measurement Marker Having Arbitrary Shape)

Further, the display controller 8 may cause the display 12 to display a first measurement marker 135 and a second measurement marker 235, which surround desired ranges and have arbitrary shapes, on the tomographic image 100 and the tomographic image 200, respectively. For example, when the operator designates an arbitrary shape surrounding a desired range on the tomographic image 100 by using the operation part 13, the display controller 8 causes the display 12 to display the first measurement marker 135 having a shape designated by the operation part 13, on the tomographic image 100.

Moreover, the display controller 8 controls to display, on the tomographic image 200, the second measurement marker 235 having the same shape as the shape of the first measurement marker 135 in relatively the same position as the first measurement marker 135. The measuring part 10 receives coordinate information of the first measurement marker 135 from the display controller 8, and obtains the perimeter of the shape indicated by the first measurement marker 135 and the area of the inside of the shape. The display controller 8 causes the display 12 to display the perimeter and the area as the measurement values. By thus using a measurement marker having an arbitrary shape, it is possible to designate a desired range on a tomographic image and obtain the perimeter and area of the range. For example, by surrounding a site to be measured having a complicated shape with this measurement marker, it is possible to obtain the perimeter and area of the site.

Further, in a case that the distance between two points is to be obtained by using a first measurement marker 131 (a second measurement marker 231) having a major marker and a minor marker, the measuring part 10 may set a spline curve between the two points and obtain the length of the spline curve. Moreover, also in a case that the distance between two points composing a first measurement marker 132 (a second measurement marker 232) is to be obtained, the measuring part 10 may set another spline curve between the two points and obtain the length of the spline curve. In a case that a spline curve is thus set, the display controller 8 controls to display a marker representing the shape of the spline curve between the major marker and the minor marker.

(Superimposed Image of B-Mode Image and Color Doppler Image)

Figure 12:
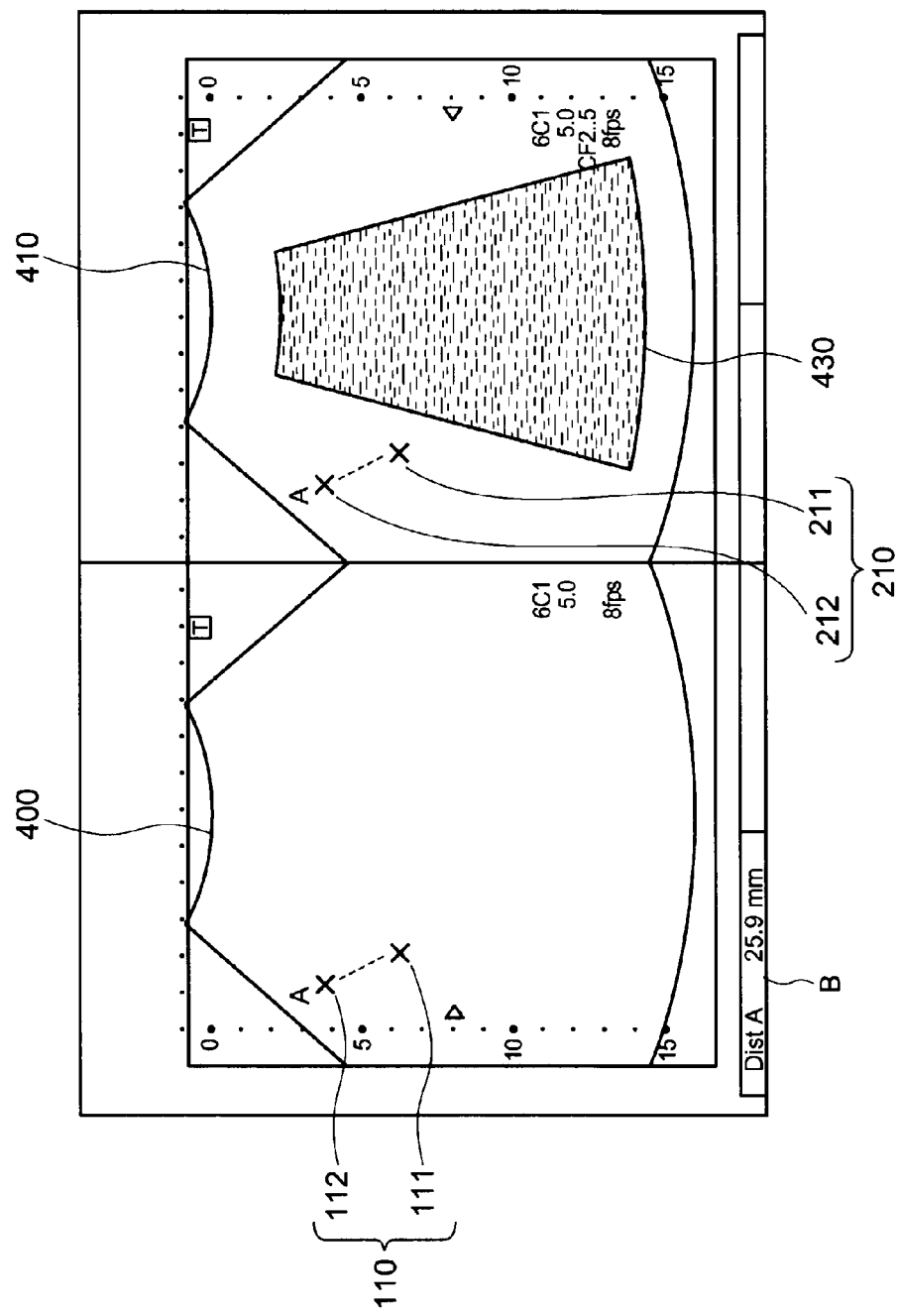
FIG. 12 is a view showing an example of a screen displaying measurement markers on a screen displaying a tomographic image and a superimposed image side by side.

Further, a measurement marker may be displayed on a superimposed image in which a B-mode image obtained by imaging in the B-mode and a color Doppler image obtained by imaging in the color Doppler mode are superimposed on each other. An example of a superimposed image on which the measurement marker is superimposed is shown in FIG. 12. FIG. 12 is a view showing an example of a screen displaying a measurement marker on a screen displaying a tomographic image and a superimposed image side by side. The display controller 8 causes the display 12 to display a tomographic image 400 obtained by imaging in the B-mode. Moreover, the display controller 8 causes the display 12 to display a superimposed image in which a tomographic image 410 obtained by imaging in the B-mode and a color Doppler image 430 obtained by imaging in the color Doppler mode. Then, as in the aforementioned process, the display controller 8 causes the display 12 to display the first measurement marker 110 in a state superimposed on the tomographic image 400 and display the second measurement marker 210 in relatively the same position as the first measurement marker 110 on the superimposed image. Also in this case, the measuring part 10 obtains the distance between two points designated by the first measurement marker 110, and the display controller 8 controls to display the distance as the measurement value in the display field B.

(Display of Measurement Marker on Reversed Image)

Figure 13:
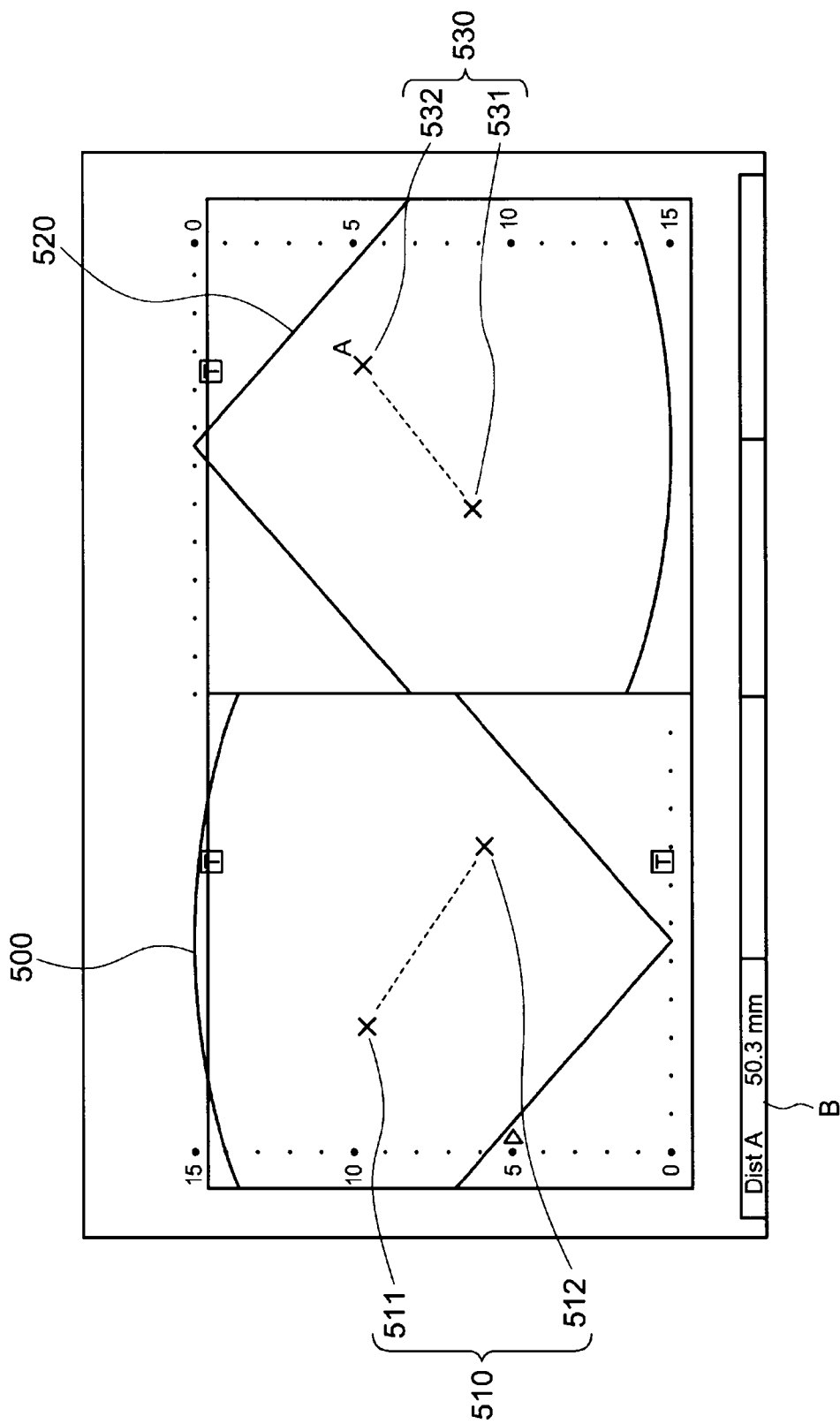
FIG. 13 is a view showing an example of a screen displaying measurement markers on a vertically reversed tomographic image.

Further, one of the two ultrasound images displayed on the display 12 may be reversed horizontally or vertically to be displayed. In this case, the display controller 8 controls to display the measurement markers in relatively the same positions on the two ultrasound images, respectively, with reference to the coordinate system on the real space. A vertically reversed ultrasound image is shown in FIG. 13. FIG. 13 is a view showing an example of a screen displaying a measurement marker on the vertically reversed tomographic image.

As shown in FIG. 13, the display controller 8 causes the display 12 to simultaneously display a tomographic image 500 and a tomographic image 520 side by side. Here, the display controller 8 vertically reverses the tomographic image 500 with respect to the tomographic image 520, and causes the display 12 to display the tomographic image 500 and the tomographic image 520. On the screen of the display 12, the upper portion of the tomographic image 520 is shallower, and the lower portion of the tomographic image 520 is deeper. On the other hand, the upper portion of the tomographic image 500 is deeper, and the lower portion thereof is shallower.

In this case, the display controller 8 controls to display the measurement markers in relatively the same positions on the real space on the tomographic image 500 and the tomographic image 520. For example, the operator designates, by using the operation part 13, the positions of a first major marker 511 and a first minor marker 512 composing a first measurement marker 510. The display controller 8 controls to display the first major marker 511 and the first minor marker 512 in the positions designated with the operation part 13 on the tomographic image 500. Moreover, the display controller 8 specifies the position on the real space of the first measurement marker 510 on the tomographic image 500. Then, the display controller 8 controls to display a second measurement marker 530 in a position on the tomographic image 520 corresponding to relatively the same position on the real space as the position on the real space of the first measurement marker 510.

To be specific, the display controller 8 controls to display a second major marker 531 in a position on the tomographic image 520 corresponding to the same depth on the real space as the depth of the first major marker 511 shown on the tomographic image 500. Moreover, the display controller 8 controls to display the second major marker 531 in a position on the tomographic image 520 corresponding to the same position in the scanning direction on the real space as the position in the scanning direction of the first major marker 511 shown on the tomographic image 500. Similarly, the display controller 8 controls to display a first minor marker 512 and a second minor marker 532 in the same positions on the real space on the tomographic image 500 and the tomographic image 520.

Then, the measuring part 10 receives coordinate information representing the position on the real space of the first measurement marker 510 from the display controller 8, and obtains the distance between the first major marker 511 and the first minor marker 512 as the measurement value.

The display controller 8 controls to display the measurement value in the display field B of the display 12.

Figure 14:
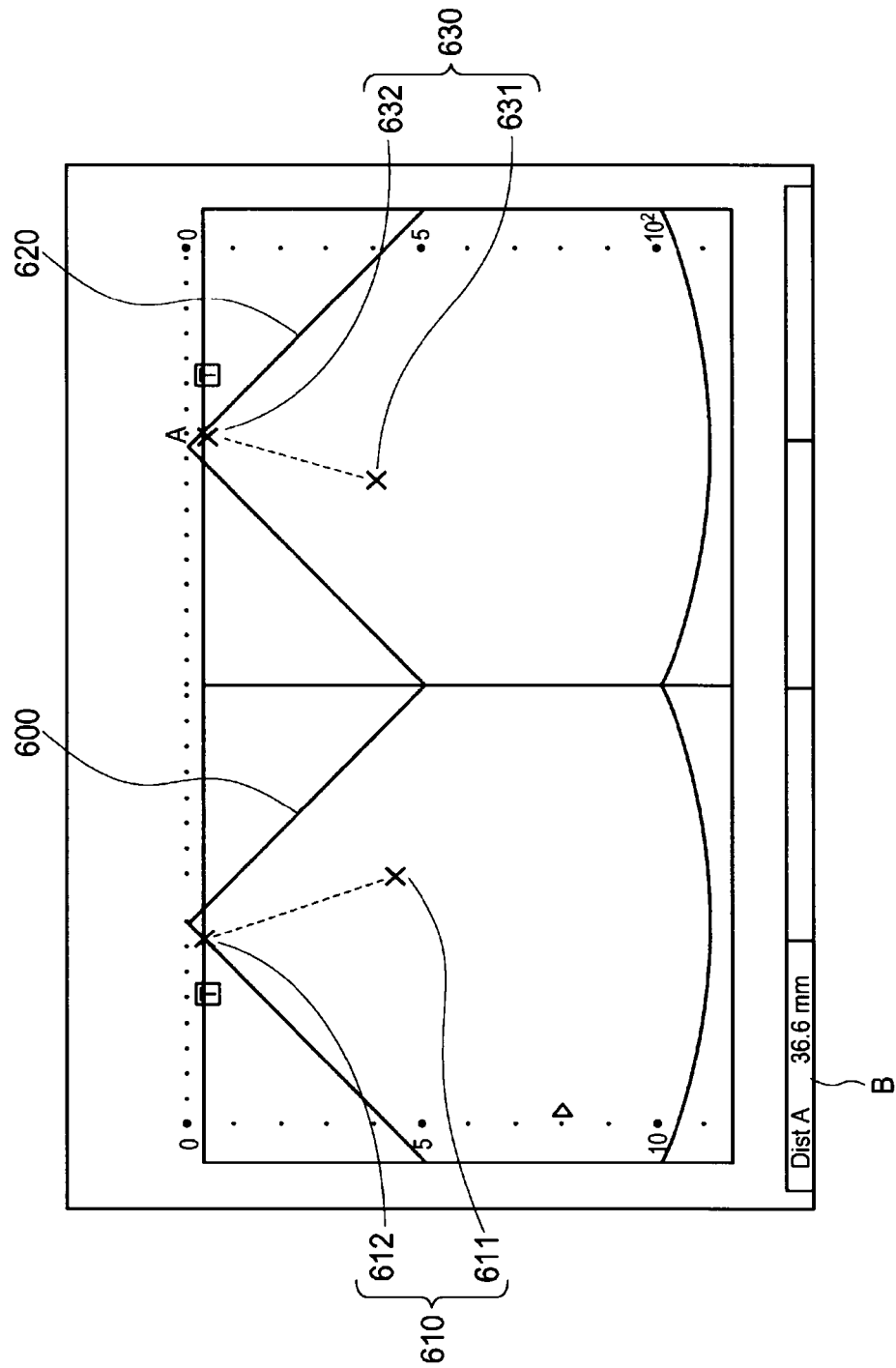
FIG. 14 is a view showing an example of a screen displaying measurement markers on a horizontally reversed tomographic image.

Further, for a horizontally reversed ultrasound image, it is possible to obtain quantitative information in the same manner as for the vertically reversed ultrasound image. The horizontally reversed ultrasound image is shown in FIG. 14. FIG. 14 is a view showing an example of a screen displaying a measurement marker on the horizontally reversed tomographic image.

As shown in FIG. 14, the display controller 8 controls to simultaneously display a tomographic image 600 and a tomographic image 620 side by side on the display 12. For example, the display controller 8 horizontally reverses the tomographic image 600 with respect to the tomographic image 620, and controls to display the tomographic image 600 and the tomographic image 620 on the display 12.

Also in this case, the display controller 8 controls to display measurement markers in relatively the same positions on the real space on the tomographic image 600 and the tomographic image 620. For example, the operator designates, by using the operation part 13, the positions of a first major marker 611 and a first minor marker 612 composing a first measurement marker 610. The display controller 8 controls to display the first major marker 611 and the first minor marker 612 in the positions designated with the operation part 13 on the tomographic image 600. Moreover, the display controller 8 specifies the position on the real space of the first measurement marker 610 on the tomographic image 600. Then, the display controller 8 controls to display a second measurement marker 630 in a position on the tomographic image 620 corresponding to relatively the same position on the real space as the position of the first measurement marker 610 on the real space. Consequently, a second major marker 631 is displayed in the same position as the position on the real space of the first major marker 611, on the tomographic image 620. Similarly, a second minor marker 632 is displayed in the same position as the position on the real space of the first minor marker 612, on the tomographic image 620.

Then, the measuring part 10 receives coordinate information representing the position on the real space of the first measurement marker 610 from the display controller 8, and obtains the distance between the first major marker 611 and the first minor marker 612 as the measurement value.

The display controller 8 controls to display the measurement value in the display field B of the display 12.

Thus, the ultrasound imaging apparatus 1 according to the present embodiment simultaneously displays a plurality of ultrasound images side by side and displays measurement markers in relatively the same positions on the plurality of ultrasound images, respectively, on the images, whereby the operator can easily specify the positions corresponding to each other on the plurality of images. Consequently, it becomes possible to measure a measurement target in each of the corresponding positions on the plurality of ultrasound images. For example, the ultrasound imaging apparatus simultaneously displays a body tissue image and a harmonic image side by side, and displays measurement markers in relatively the same positions on the respective images, whereby the operator can easily grasp the positional relation between a lesion part such as tumor and a contrast site. Then, it becomes possible to obtain quantitative information of tissue in relatively the same positions on the body tissue image and the harmonic image.

(Image Processor 14)

Next, the image processor 14 will be described. The image processor 14 includes a reference-image generator 15 and a tracking part 16. The image processor 14 executes pattern matching on a plurality of ultrasound image data acquired at different times, thereby obtaining the position of tissue of a specified range including a position where the measurement marker is superimposed, in each of the plurality of image data. Thus, the image processor 14 tracks at times the position of the measurement marker designated on a certain ultrasound image. The image processor 14 is equivalent to an "image processor" of the present invention. The ultrasound imaging apparatus 1 may be configured not to include the image processor 14.

In the case of tracking the position of the measurement marker, the ultrasound imaging apparatus 1 can include the image processor 14. The reference-image generator 15 and the tracking part 16 will be described below.

(Reference-Image Generator 15)

The reference-image generator 15 receives coordinate information representing the position of a measurement marker on an ultrasound image from the display controller 8. Moreover, the reference-image generator 15 reads ultrasound image data acquired at each time from the image storage 7.

Then, the reference-image generator 15 generates image data representing tissue of a specified range including the position of the measurement marker as reference-image data, based on ultrasound image data in which the measurement marker is set. For example, the reference-image generator 15 sets a rectangularly-shaped range including the position of the measurement marker and having a specified size, and generates reference-image data representing tissue in the rectangularly-shaped range from the ultrasound image data in which the measurement marker is set.

(Tracking Part 16)

The tracking part 16 executes pattern matching on the reference-image data and the ultrasound image data acquired at each time, thereby specifying the position of the tissue of the specified range represented in the reference-image data, in each of the plurality of ultrasound image data. By specifying the position of the tissue of the specified range in this manner, the tracking part 16 specifies the position of the measurement marker in each of the plurality of ultrasound image data. Thus, the tracking part 16 tracks the position of the measurement marker at times. As the pattern matching, for example, the template matching method (the block matching method) can be used. To be specific, the tracking part 16 obtains a subtraction between a reference image and an ultrasound image, and obtains a position with the least subtraction, thereby tracking the position of the measurement marker.

The tracking part 16 outputs coordinate information representing the position of the measurement marker at each time to the display controller 8.

The display controller 8 reads ultrasound image data acquired at each time from the image storage 7, and causes the display 12 to display the measurement marker at each time in a state superimposed on the ultrasound image acquired at each time.

By tracking the position of the measurement marker as described above, even if a measurement target is moved and the position thereof is changed by breathing or beating of a patient, the measurement marker designated by the operator automatically follows the measurement target and keeps designating the measurement target.

Figure 15:
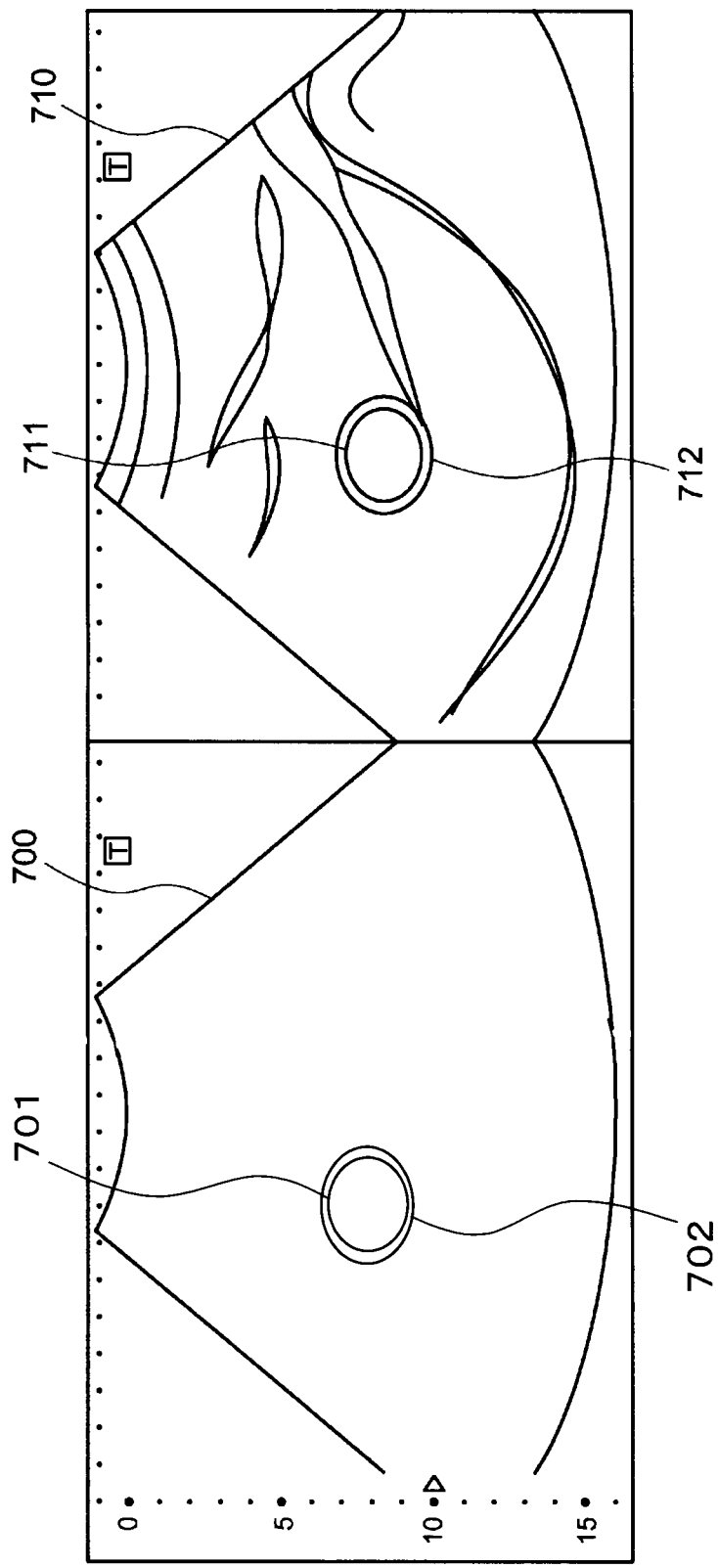
FIG. 15 is a view showing an example of a screen displaying measurement markers on a screen displaying a body tissue image and a harmonic image side by side.
Figure 16:
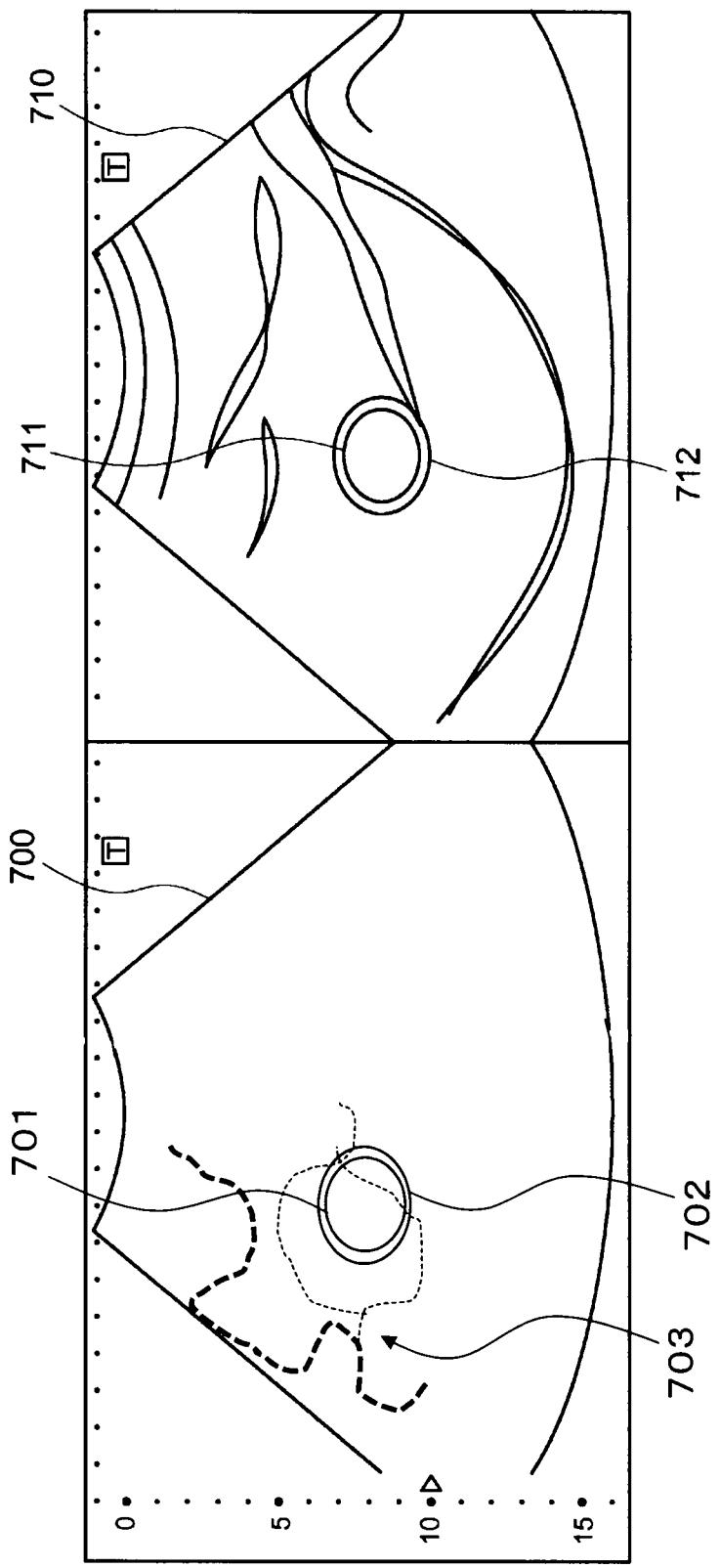
FIG. 16 is a view showing an example of a screen displaying measurement markers on a screen displaying a body tissue image and a harmonic image side by side.

As an example, a case of simultaneously displaying a body tissue image generated based on fundamental waves and a harmonic image generated based on harmonic waves side by side and setting measurement markers on both the images will be described with reference to FIGS. 15 and 16. FIGS. 15 and 16 are views showing an example of a screen displaying the measurement markers on a screen displaying the body tissue image and the harmonic image side by side.

As shown in FIG. 15, the display controller 8 controls to simultaneously display a body tissue image 710 based on fundamental waves and a harmonic image 700 based on harmonic waves side by side on the display 12. A tumor 711 is shown on the body tissue image 710, and a tumor 701 is shown on the harmonic image 700. As described above, the operator moves the measurement marker to a desired position by using the operation part 13. As an example, a circularly-shaped measurement marker is used. The display controller 8 causes the display 12 to display a circularly-shaped first measurement marker 712 on the body tissue image 710. As described above, the display controller 8 controls to display the first measurement marker 712 and a second measurement marker 702 in relatively the same positions on the body tissue image 710 and the harmonic image 700. The operator moves the first measurement marker 712 to a desired position by using the operations part 13, and changes the size of the marker to an arbitrary size. For example, by using the operation part 13, the operator moves the first measurement marker 712 to the position of the tumor 711, changes the size of the first measurement marker 712, and surrounds the tumor 711 by the first measurement marker 712. The display controller 8 causes the display 12 to display the first measurement marker 712 surrounding the tumor 711 in accordance with the movement amount outputted from the operation part 13.

Moreover, the display controller 8 controls to display the second measurement marker 702 in relatively the same position as the first measurement maker 712.

As described above, when the position of a tumor is designated by the first measurement maker 712, coordinate information representing the position of the first measurement marker 712 on the body tissue image 710 is outputted to the reference-image generator 15. The reference-image generator 15 generates reference-image data representing tissue of a specified range including the position of the first measurement marker 712, based on body tissue image data in which the first measurement marker 712 is set. A body tissue image has higher visibility than a harmonic image, and shows little change in image even if a contrast agent flows in. Before a contrast agent is injected into the subject, the morphology of tissue is not shown in a harmonic image. Accordingly, a body tissue image is more suitable for pattern matching than a harmonic image, and therefore, reference-image data is generated from body tissue image data.

The tracking part 16 reads the body tissue image data acquired at each time, from the image storage 7. Then, the tracking part 16 executes pattern matching on the reference-image data and the body tissue image data acquired at each time, thereby specifying the position of tissue of a specified range represented in the reference-image data, in the body tissue image data at each time. Thus, by specifying the position of tissue of a specified range, the tracking part 16 specifies the position of the first measurement marker 712 in each of a plurality of body tissue image data.

The tracking part 16 outputs coordinate information representing the position of the first measurement marker 712 at each time to the display controller 8. The display controller 8 reads the body tissue image data and the harmonic image data that have been acquired at each time, from the image storage 7. The display controller 8 causes the display 12 to simultaneously display a body tissue image and a harmonic image that have been acquired at equal times side by side. Then, in accordance with the order of acquisition times, the display controller 8 updates the body tissue image and the harmonic image that have been acquired at each time, and causes the display 12 to display. At this moment, the display controller 8 causes the display 12 to display the first measurement marker 712 at each time obtained by the tracking part 16 on the body tissue image 710 acquired at each time. Besides, the display controller 8 controls to display the second measurement marker 702 in relatively the same position as the first measurement marker 712 on the harmonic image 700 acquired at each time. Additionally, the display controller 8 controls to display the second measurement marker 702 in relatively the same position as the first measurement marker 712 on the harmonic image 700 acquired at each time.

By thus tracking the position of the measurement marker, it is possible to specify the position of the tumor shown in the body tissue image and the position of the contrast agent shown in the harmonic image at each time.

Consequently, the operator can easily grasp the positional relation between the tumor and the contrast agent.

Furthermore, the measuring part 10 receives coordinate information of the first measurement marker 712 at each time from the display controller 8, and obtains the perimeter and area of the measurement target indicated by the first measurement marker 712 at each time. Then, the display controller 8 causes the display 12 to display the perimeter and area of the measurement target at each time. By thus tracking the measurement marker by the tracking part 16, it becomes possible to obtain quantitative information of the measurement target at each time.

Further, as in the harmonic image 700 shown in FIG. 16, when the contrast agent injected into the subject flows into the vessels, a vessel 703 in which the contrast agent flows is enhanced and displayed. In the prior art, it is difficult to grasp the positional relation between the tumor 711 shown in the body tissue image 710 and the vessel 703 (the vessel 703 enhanced by the contrast agent) shown in the harmonic image 700. In other words, in the conventional art, the measurement calipers are not displayed in relatively the same positions on the body tissue image 710 and the harmonic image 700, so that it is difficult to grasp the positional relation between the tumor 711 and the vessel 703.

On the contrary, in this embodiment, the display controller 8 controls to display the first measurement marker 712 and the second measurement marker 702 in relatively the same positions on the body tissue image 710 and the harmonic image 700. Consequently, it becomes possible to easily grasp the positional relation between the tumor 711 shown in the body tissue image 710 and the vessel 703 (the vessel 703 enhanced by the contrast agent) shown in the harmonic image 700.

(Mesh Measurement Marker)

Figure 17:
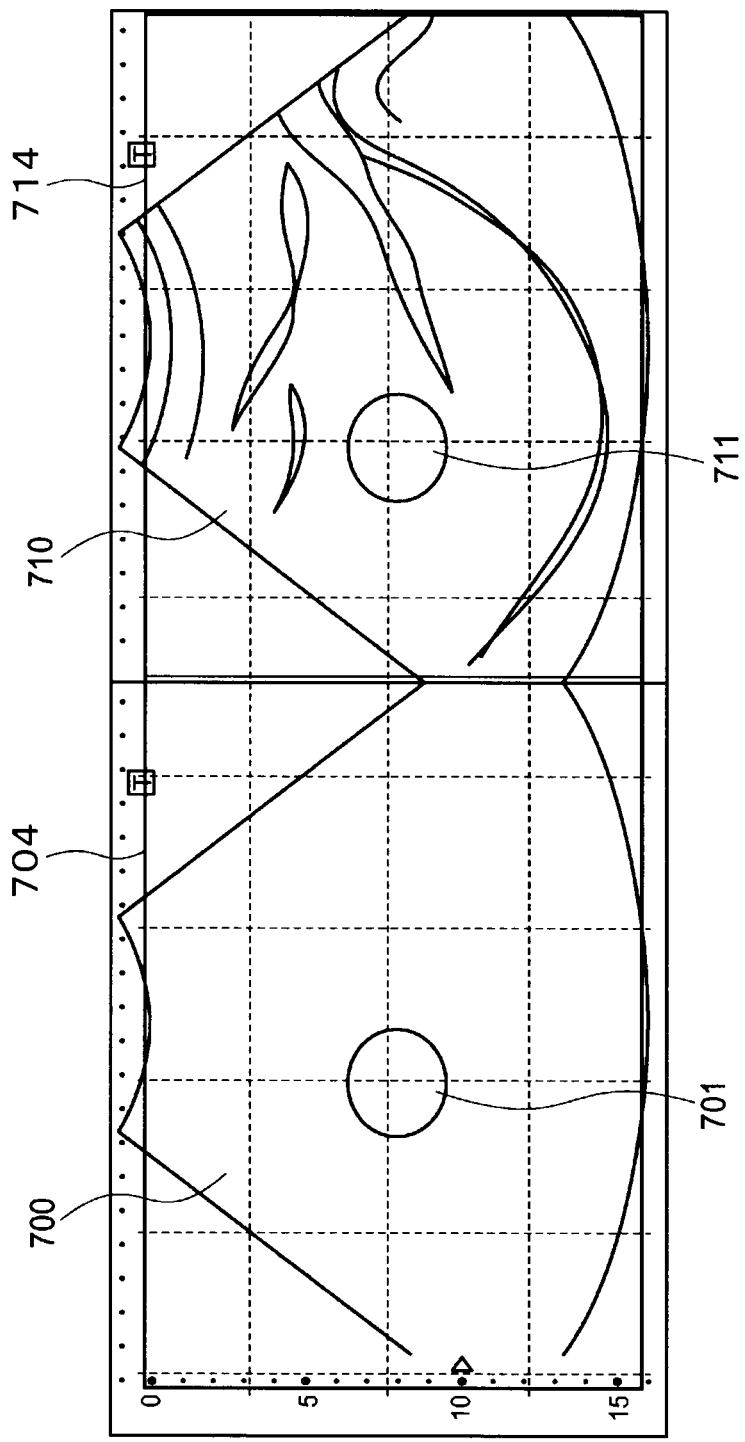
FIG. 17 is a view showing an example of a screen displaying measurement markers on a screen displaying two tomographic images side by side.

Further, a mesh measurement marker covering the whole region of each ultrasound image may be displayed. This measurement marker is shown in FIG. 17. FIG. 17 is an example of a screen displaying the measurement marker on a screen displaying two tomographic images side by side.

For example, the display controller 8 causes the display 12 to simultaneously display the body tissue image 710 based on fundamental waves and the harmonic image 700 based on harmonic waves side by side.

Then, the display controller 8 causes the display 12 to display a first mesh measurement marker 714 covering the whole region of the body tissue image 710 on the body tissue image 710. Similarly, the display controller 8 causes the display 12 to display a second mesh measurement marker 704 covering the whole region of the harmonic image 700 on the harmonic image 700 on the display 12. At this moment, the display controller 8 controls to display the position of each of lines forming the mesh of the measurement marker in relatively the same positions on the body tissue image 710 and the harmonic image 700. To be specific, the display controller 8 controls to display the mesh of the first measurement marker 714 on the body tissue image 710 and the mesh of the second measurement marker 704 on the harmonic image 700 in relatively the same positions on the real space, with reference to the coordinate system on the real space. For example, the display controller 8 controls to display the mesh of the first measurement marker 714 and the mesh of the second measurement marker 704 in the same positions in depth and scanning direction.

As described above, mesh measurement markers covering the whole regions of images are displayed on the body tissue image 710 and the harmonic image 700, and further, the meshes are displayed in relatively the same positions on the body tissue image 710 and the harmonic image 700, whereby the operator can easily grasp the positional relation of a tumor and a contrast agent with reference to the mesh.

Further, in the case of simultaneous display of a harmonic image and a body tissue image, if the position of the subject or the ultrasound probe 2 is displaced, scan with ultrasound waves will be executed in the displaced position. Consequently, in the harmonic image and the body tissue image, images of sites in the displaced positions are shown. Therefore, a measurement marker set on each of the harmonic image and the body tissue image will be set in a position displaced from an initially set position (a desired measurement target) on each of the images. As a result, it becomes difficult to keep designating the desired measurement target with the measurement marker.

Accordingly, in this embodiment, the display position of the harmonic image on the display 12 is corrected depending on the displacement amount, and the displacement amount is offset to display the harmonic image, whereby the site shown in the harmonic image is displayed in a fixed position on the display 12. Consequently, even if the position of the subject or the ultrasound probe 2 is displaced, a state in which the measurement marker is set in the initially set position (the desired measurement target) is maintained.

On the other hand, since the image of the site in the displaced position is shown in the body tissue image, the measurement marker remains set in the position displaced from the initially set position (the desired measurement target).

Accordingly, in this embodiment, the display position of the measurement marker set on the body tissue image is corrected depending on the displacement amount, and the displacement amount is offset to display the measurement marker on the body tissue image (a first correction method).

Although the image of the site in the displaced position is shown in the body tissue image, the measurement marker is displayed in the display position corrected depending on the displacement amount, so that a state in which the measurement marker is set in the initially set position (the desired measurement target) is maintained on the body tissue image.

Alternatively, as in the case of the harmonic image, the display position of the body tissue image on the display 12 is corrected depending on the displacement amount and the displacement amount is offset to display the body tissue image (a second correction method). Consequently, since the site shown in the body tissue image is displayed in a fixed display position on the display 12, a state in which the measurement marker is set in the initially set position (the desired measurement target) is maintained on the body tissue image.

Figure 18:
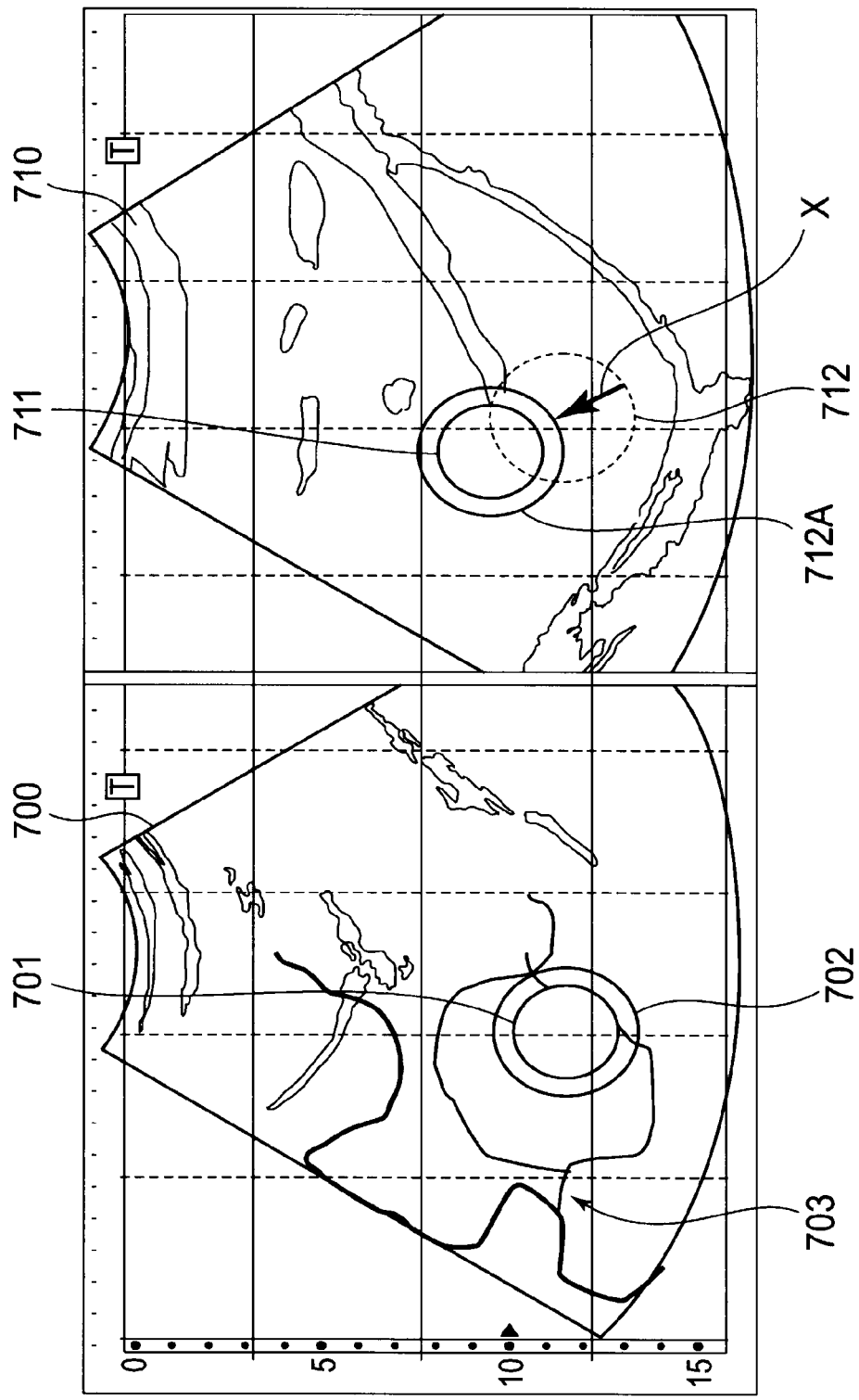
FIG. 18 is a view showing an example of a screen displaying measurement markers on a screen displaying a body tissue image and a harmonic image side by side.
Figure 19:
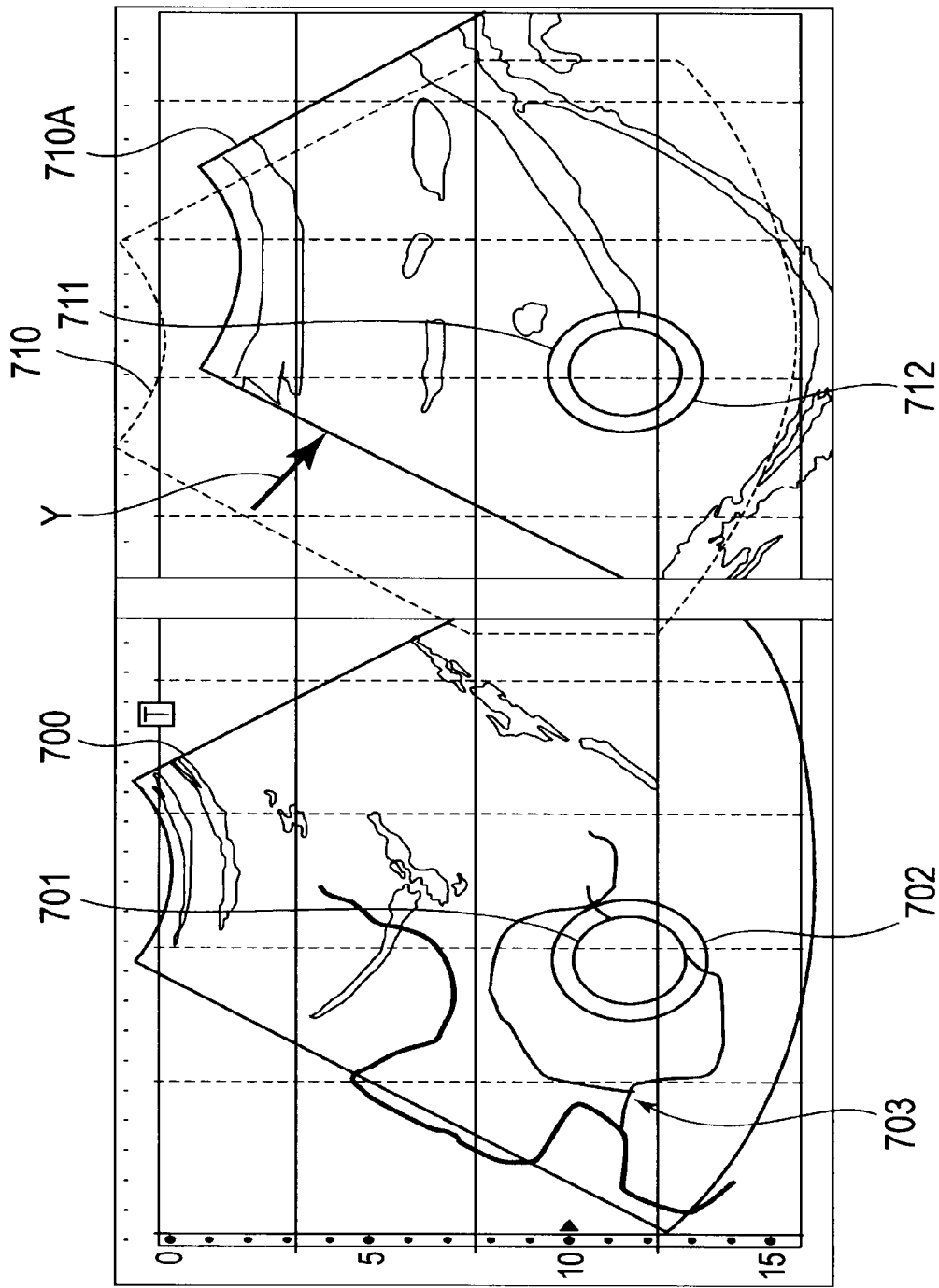
FIG. 19 is a view showing an example of a screen displaying measurement markers on a screen displaying a body tissue image and a harmonic image side by side.

A specific example of correction of the displacement amount will be described below with reference to FIGS. 18 and 19. FIGS. 18 and 19 are views showing an example of a screen displaying a measurement marker on a screen displaying a body tissue image and a harmonic image side by side.

(First Correction Method)

First, the aforementioned first correction method will be described with reference to FIG. 18.

As shown in FIG. 18, the display controller 8 causes the display 12 to simultaneously display the body tissue image 710 based on fundamental waves and the harmonic image based on harmonic waves side by side. The tumor 711 is shown in the body tissue image 710. As an example, the display controller 8 causes the display 12 to display the first circular measurement marker 712 (a marker indicated by a broken line) in a state superimposed on the body tissue image 710 and display the second circular measurement marker 702 in a state superimposed on the harmonic image 700. When a contrast agent injected into the subject flows in, the vessel 703 in which the contrast agent flows is enhanced and displayed on the harmonic image 700.

The display controller 8 controls to display the first measurement marker 712 and the second measurement marker 702 in relatively the same positions on the body tissue image 710 and the harmonic image 700. For example, in response to an operator's instruction, the display controller 8 causes the display 12 to display the first measurement marker 712 surrounding the tumor 711 on the body tissue image 710. Moreover, the display controller 8 causes the display 12 to display the second measurement marker 702 on the harmonic image 700, in relatively the same position as the first measurement marker 712.

The image processor 14 reads harmonic image data acquired at each time from the image storage 7. Then, the image processor 14 executes pattern matching on the harmonic image data acquired at each time, thereby specifying the position of the vessel 703 at each time. That is to say, the image processor 14 sets the vessel 703 represented in the harmonic image data acquired at each time as a tracking target to track the position of the vessel 703 at each time by the pattern matching. The image processor 14 tracks the position of the vessel 703 represented in the harmonic image data, thereby detecting the position displacement (the direction and amount of the position displacement) of the vessel 703 represented in the harmonic image data, and outputting position displacement information (vector information) representing the direction and the amount of the position displacement to the display controller 8. For example, in a case that the position of the vessel 703 represented in the harmonic image data is displaced as a result of displacement of the position of a region scanned with ultrasound waves due to the movement of the subject, the image processor 14 tracks the position of the vessel 703 represented in the harmonic image data, thereby detecting the displacement of the position. As a method of detecting position displacement, for example, the method described in Japanese Unexamined Patent Publication No. 2007-330764 can be employed.

When receiving the position displacement information (vector information) from the image processor 14, the display controller 8 corrects the display position of the harmonic image 700 in accordance with the position displacement information, and controls to display on the display 12.

To be specific, the display controller 8 controls to display the harmonic image 700 in a display position displaced by the same distance as the displacement amount in the direction opposite to the position displacement direction. Consequently, the position displacement is offset, and a site shown in the harmonic image 700 can be displayed in a fixed display position on the display 12. In this state, the display controller 8 fixes the display position, and causes the display 12 to display the second measurement marker 702 on the harmonic image 700. Consequently, the second measurement marker 702 will keep designating the initially set position (the desired measurement target) on the harmonic image 700.

Further, the display controller 8 corrects the display position of the first measurement marker 712 (the marker indicated by the broken line) on the body tissue image 710 in accordance with the position displacement information, and controls to display on the display 12. To be specific, the display controller 8 controls to display the first measurement marker in a display position displaced by the same distance as the displacement amount in the same direction as the position displacement direction represented by the position displacement information on the body tissue image 710. In the example shown in FIG. 18, the display controller 8 controls to display a post-correction first measurement marker 712A in a display position where the pre-correction first measurement marker 712 (the marker indicated by the broken line) is displaced by the same distance as the displacement amount represented by the position displacement information in an arrow X direction (the same direction as the position displacement direction). Consequently, the post-correction first measurement marker 712A will keep designating the initially set position (the desired measurement target) on the body tissue image 710.

By the correction process described above, even if the position of the subject or the ultrasound probe 2 is displaced, it is possible to display the measurement markers in relatively the same positions on the body tissue image 710 and the harmonic image 700.

(Second Correction Method)

Next, the aforementioned second correction method will be described with reference to FIG. 19.

As shown in FIG. 19, the display controller 8 causes the display 12 to display the body tissue image 710 based on fundamental waves (an image framed by a broken line) and the harmonic image 700 based on harmonic waves side by side. The tumor 711 is shown in the body tissue image 710. As described above, the display controller 8 causes the display 12 to display the first measurement marker 712 surrounding the tumor 711 on the body tissue image 710 (the image framed by the broken line), and causes the display 12 to display the second measurement marker 702 on the harmonic image 700, in relatively the same position as the first measurement marker 712.

As in the aforementioned first correction method, the image processor 14 reads harmonic image data acquired at each time from the image storage 7.

Then, the image processor 14 executes pattern matching on the harmonic image data acquired at each time, thereby specifying the position of the vessel 703 at each time. That is to say, the image processor 14 sets the vessel 703 represented in the harmonic image data acquired at each time as a tracking target, and tracks the position of the vessel 703 at each time by the pattern matching. The image processor 14 tracks the position of the vessel 703 represented in the harmonic image data, thereby detecting the position displacement (the direction and amount of the position displacement) of the vessel 703 represented in the harmonic image data, and outputting position displacement information (vector information) representing the direction and the amount of the position displacement to the display controller 8.

When receiving the position displacement information (vector information) from the image processor 14, as in the aforementioned first correction method, the display controller 8 controls to display the harmonic image 700 in a display position displaced by the same distance as the displacement amount in the direction opposite to the position displacement direction. Consequently, the position displacement is offset, and a site shown in the harmonic image 700 can be displayed in a fixed display position on the display 12. In this state, the display controller 8 fixes the display position, and causes the display 12 to display the second measurement marker 702 in a state superimposed on the harmonic image 700. Consequently, the second measurement marker 702 will keep designating the initially set position (the desired measurement target) on the harmonic image 700.

Further, the display controller 8 corrects the display position of the body tissue image 710 (the image framed by the broken line) in accordance with the position displacement information, and controls to display on the display 12. To be specific, the display controller 8 controls to display the body tissue image in a display position displaced by the same distance as the displacement amount in the opposite direction to the position displacement direction represented by the position displacement information. In the example shown in FIG. 19, the display controller 8 controls to display a post-correction body tissue image 710A in a display position where the pre-correction body tissue image 710 (the image framed by the broken line) is displaced by the same distance as the displacement amount represented by the position displacement information in an arrow Y direction (the opposite direction to the position displacement direction). In this state, the display controller 8 fixes the display position, and causes the display 12 to display the first measurement marker 712 in a state superimposed on the body tissue image 710A. Consequently, the first measurement marker 712 will keep designating the initially set position (the desired measurement target) on the post-correction body tissue image 710A.

By the correction process described above, even if the position of the subject or the ultrasound probe 2 is displaced, it is possible to display the measurement markers in relatively the same positions on the body tissue image 710 and the harmonic image 700.

(Display of Previous Image)

The display controller 8 may attach identification information representing simultaneous display to a plurality of ultrasound image data simultaneously displayed side by side on the display 12 and cause the image storage 7 to store as previous image data. In the case of causing the display 12 to simultaneously display, side by side, a plurality of previous images based on the previous image data with the identification information attached, the display controller 8 causes the display 12 to display measurement markers in relatively the same positions on the respective previous images. Thus, in the case of simultaneously displaying a plurality of previous images side by side, it is also possible to display the measurement markers in relatively the same positions and obtain quantitative information in corresponding positions.

The display controller 8 may cause the display 12 to display previous images side by side, or may cause the display 12 to display a previous image and an ultrasound image acquired in real time side by side. In the case of simultaneously displaying a plurality of previous images side by side, it is preferred that the display controller 8 causes the display 12 to display a measurement marker to be operated by the operator so as to be distinguishable from other measurement markers. For example, it is preferred that the display controller 8 causes the display 12 to display the measurement marker to be operated in color and size different from those of other measurement markers. Moreover, in the case of simultaneously displaying a previous image and an ultrasound image acquired in real time side by side, it is preferred to cause the display 12 to display a measurement marker displayed on the previous image or the real-time image so as to be distinguishable from other measurement markers. Consequently, the operator can differentiate and recognize the previous image and the real-time image from among the plurality of images displayed on the display 12.

Each of the image generator 6, the display controller 8, the measuring part 10 and the image processor 14 may be composed of a not-shown CPU (Central Processing Unit) and a not-shown storage device such as a ROM (Read Only Memory), a RAM (Random Access Memory) and an HDD (Hard Disk Drive). The storage device stores an image generation program for executing the function of the image generator 6, a display control program for executing the function of the display controller 8, a measurement program for executing the function of the measuring part 10, and an image processing program for executing the function of the image processor 14. Moreover, the image processing program includes a reference-image generation program for executing the function of the reference-image generator 15, and a tracking program for executing the function of the tracking part 16.

By execution of the image generation program, the CPU generates ultrasound image data such as tomographic image data based on signals acquired in transmission/reception of ultrasound waves. Moreover, by execution of a marker generation program, the CPU generates data representing the measurement marker. Moreover, by execution of the display control program, the CPU causes the display 12 to display an ultrasound image based on ultrasound image data, and further, controls to display the measurement marker in a state superimposed on the ultrasound image.

Moreover, by execution of the reference-image generation program, the CPU generates reference-image data representing a specified range including a position on which the measurement marker is superimposed.

Moreover, by execution of the tracking program, the CPU specifies the position of the measurement marker in each of the plurality of ultrasound image data.

(Medical Image processing Apparatus)

Further, a medical image processing apparatus that simultaneously displays a plurality of ultrasound images side by side may be disposed outside the ultrasound imaging apparatus. This medical image processing apparatus includes the aforementioned image storage 7, display controller 8, user interface (UI) 11, measuring part 10, and image processor 14. In a case that tracking of the measurement marker is not executed, the image processor 14 may be eliminated from the medical image processing apparatus. The medical image processing apparatus acquires a plurality of ultrasound image data from the external ultrasound imaging apparatus, simultaneously displays a plurality of ultrasound images side by side, and displays measurement markers in relatively the same positions on the respective ultrasound images.

This medical image processing apparatus can also produce the same actions and effects as the aforementioned ultrasound imaging apparatus 1.

What is claimed is:

1. An ultrasound imaging apparatus, comprising:
an imaging part configured to acquire a plurality of sets of ultrasound image data by sequentially imaging a subject with ultrasound waves at a corresponding plurality of different times; and
a display controller configured to cause a display to display, side by side in respective display regions, a plurality of ultrasound images based on the plurality of sets of ultrasound image data acquired by the imaging part at the corresponding plurality of different times, and cause the display to display markers in a state superimposed on the plurality of ultrasound images, respectively, in the same corresponding positions in each of the ultrasound images with respect to a coordinate system in a real space in which the plurality of sets of ultrasound image data were acquired, even if the display magnification rate of the plurality of ultrasound images is different.

2. The ultrasound imaging apparatus according to claim 1, further comprising:

an image storage configured to attach, to the plurality of sets of ultrasound image data representing the plurality of ultrasound images displayed side by side on the display, identification information representing the display side by side, and store the plurality of sets of ultrasound image data as previous ultrasound image data, wherein the display controller is configured to cause the display to display a plurality of sets of previous ultrasound images based on the plurality of previous ultrasound image data, and to cause the display to display the markers in a state superimposed on the respective previous ultrasound images in the same corresponding positions in each of the previous ultrasound images.

3. The ultrasound imaging apparatus according to claim 1, wherein:

the apparatus further includes an image processor configured to obtain, as reference-image data, image data representing tissue of a specified range including a position where the marker is superimposed and to execute pattern matching on the reference-image data and the plurality of sets of ultrasound image data sequentially acquired, thereby specifying a position of the tissue of the specified range represented in the reference-image data in each of the plurality of sets of ultrasound image data, and specifying the position where the marker is superimposed on the plurality of ultrasound images from the specification; and the display controller, in accordance with the positions of the markers specified by the image processor, is configured to cause the display to display the markers in a state superimposed on the plurality of ultrasound images, respectively, in the same corresponding positions in each of the ultrasound images.

4. The ultrasound imaging apparatus according to claim 1, further comprising:

an operation part configured to designate the marker displayed in a superimposed state on one of the plurality of ultrasound images displayed on the display, and to move the designated marker to a desired position on the one ultrasound image, wherein:

the display controller is configured to specify a position in the real space of the desired position on the one ultrasound image, and to cause the display to display the markers in a state superimposed on the ultrasound images other than the one ultrasound image, in positions on the images corresponding to positions that are the same as the specified position in the real space.

5. The ultrasound imaging apparatus according to claim 1, wherein:

the display controller causes the display to display, as the marker, a marker having a circular, elliptic, rectangular, mesh-shaped, triangular, or arbitrary curved shape.

6. The ultrasound imaging apparatus according to claim 1, wherein:

the display controller is configured to display a mesh marker having lines like a mesh, and to cause the display to display the mesh marker so that positions of the respective lines forming the mesh of the mesh marker are superimposed on the plurality of ultrasound images, respectively, in the same corresponding positions in each of the ultrasound images.

7. The ultrasound imaging apparatus according to claim 1, further comprising:

a measuring part configured to obtain quantitative information of the tissue shown in the plurality of ultrasound images in the position designated by the markers.

8. A method for displaying an ultrasound image, comprising:

acquiring a plurality of sets of ultrasound image data by sequentially imaging a subject with ultrasound waves at a corresponding plurality of different times; and displaying, side by side in respective display regions, a plurality of ultrasound images based on the plurality of sets of acquired ultrasound image data acquired at the corresponding plurality of different times, and displaying markers in a state superimposed on the plurality of ultrasound images, respectively, in the same corresponding positions in each of the ultrasound images with respect to a coordinate system in a real space in which the plurality of sets of ultrasound image data were acquired, even if the display magnification rate of the plurality of ultrasound images is different.

9. The method for displaying an ultrasound image according to claim 8, further comprising:

attaching to the plurality of sets of ultrasound image data representing the plurality of ultrasound images displayed side by side, identification information representing the display side by side, and storing the plurality of sets of ultrasound image data as previous ultrasound image data into an image storage, wherein the displaying step includes displaying a plurality of previous ultrasound images based on the plurality of previous ultrasound image data, and displaying the markers in a state superimposed on the respective previous ultrasound images in the same corresponding positions in each of the previous ultrasound images.

10. The method for displaying an ultrasound image according to claim 8, further comprising:

obtaining image data representing tissue of a specified range including a position where the marker is superimposed as reference-image data, and executing pattern matching on the reference-image data and the plurality of sets of sequentially acquired ultrasound image data, whereby a position of the tissue of the specified range represented in the reference-image data is specified in each of the plurality of sets of ultrasound image data, and the position where the marker is superimposed is specified in each of the plurality of ultrasound image from the specification, wherein the displaying step includes displaying, in accordance with the specified positions of the markers, the markers in a state superimposed on the respective ultrasound images in the same corresponding positions in each of the ultrasound images.

11. The method for displaying an ultrasound image according to claim 8, further comprising:

designating the marker displayed in a superimposed state on one of the plurality of displayed ultrasound images, and moving the designated marker to a desired position on the one ultrasound image, wherein the displaying step includes specifying a position in the real space of the desired position on the one ultrasound image, and displaying the markers in a state superimposed on the ultrasound images other than the one ultrasound image, in positions on the images corresponding to positions that are the same as the specified position in the real space.

12. The method for displaying an ultrasound image according to claim 8, wherein the displaying step comprises:

displaying a marker having a circular, elliptic, rectangular, mesh-shape, triangular, or arbitrary curved shape as the marker.

13. The method for displaying an ultrasound image according to claim 8, wherein the displaying step comprises:

displaying a mesh marker having lines like a mesh as the marker, and superimposing positions of the respective lines forming the mesh of the mesh marker on the plurality of ultrasound images, respectively, in the same corresponding positions in each of the ultrasound images.

14. The method for displaying an ultrasound image according to claim 8, further comprising:

obtaining quantitative information of the tissue shown in the plurality of ultrasound images in the position designated by the markers.

* * * * *